United States Patent [19]

Oka et al.

[11] Patent Number: 5,314,991
[45] Date of Patent: May 24, 1994

[54] **RECOMBINANT 40 KDA *DERMATOPHAGOIDES FARINAE* ALLERGEN**

[75] Inventors: Satoru Oka; Kazuhisa Ono; Seiko Shigeta; Takeshi Wada, all of Hiroshima, Japan

[73] Assignees: Fumakilla Limited, Tokyo; Hiroshima University, Hiroshima, both of Japan

[21] Appl. No.: 748,783

[22] Filed: Aug. 22, 1991

[30] Foreign Application Priority Data

Aug. 27, 1990 [JP] Japan .................................. 2-225886
Nov. 27, 1990 [JP] Japan .................................. 2-327382
Mar. 9, 1991 [JP] Japan .................................. 3-104949

[51] Int. Cl.$^5$ ..................... C07K 15/08; C07K 15/00; C07K 15/12
[52] U.S. Cl. ..................... 530/350; 530/858; 530/403; 424/88; 424/91; 435/69.3; 435/7.1; 435/69.7; 435/172.1; 536/23.4; 536/23.5
[58] Field of Search ..................... 530/300, 350, 409; 435/69.1, 4, 9; 424/91

[56] References Cited

FOREIGN PATENT DOCUMENTS 8810297 12/1988 World Int. Prop. O. .

OTHER PUBLICATIONS

Heymann, P. W. et al. (86) J. Immunol. 137: 2841–2847.
Young, R. A. et al (83) Proc. Natl. Acad. Sci USA 80: 1194–1198.
Uhlen, M. et al (90) Methods in Enzymology, 185: 129–143.
Chua et al, Int. Arch. Allergy Immunol 1990:91: 1:118–123.
Chua et al, Int. Arch. Allergy Appl. Immunol 1990:91:124–129.
Thomas et al, Int. Archs Allergy appl. Immun. 85 127–129 (1988).
Yuuki et al, Agric. Biol. Chem., 55 (5) 1233–1238, 1991.
Tovey et al, J. Exp. Med. vol. 170, Oct. 1989 1457–1462.
Chua et al, J. Exp. Med. vol. 167, Jan. 1988 pp. 175–182.
Yuuki et al, Jpn. J. Allergol, 39, (6), 557–561, 1990.

*Primary Examiner*—Christine M. Nucker
*Assistant Examiner*—M. Tuscan
*Attorney, Agent, or Firm*—Birch, Stewart, Kolasch & Birch

[57] ABSTRACT

The present invention is directed to a recombinant mite allergen obtainable by expression of a mite-body-derived gene, a gene which codes for said allergen, a mite allergen fragment, a polypeptide having an epitope contained in said allergen, an expression vector capable of expressing the gene, a bacterium, yeast or mammalian cell transformed with said expression vector, a method for producing said allergen, and a pharmaceutical composition or a diagnostic reagent for the treatment of mite allergic diseases.

16 Claims, 11 Drawing Sheets

RECOMBINANT 40 KDA *DERMATOPHAGOIDES FARINAE* ALLERGEN

FIELD OF THE INVENTION

The present invention relates to a recombinant mite allergen possessing allergen activity.

BACKGROUND OF THE INVENTION

House dust mites are important as a major cause of allergic diseases such as atopic bronchial asthma.

Traditionally, hyposensitization therapy using a causative substance of allergy has been recognized as the most important basic approach to the treatment of allergic diseases, and its efficacy has already been well established in the treatment of allergic diseases caused by unavoidable inhaled allergen such as pollenosis, house dust allergy and fungal allergy.

However, this hyposensitization therapy necessitates administration of a safe therapeutic antigen since it involves a risk of anaphylaxis due to a sensitized antigen, and investigations are being made on such a sensitized antigen.

With respect to mite allergic diseases, two mite species, namely *Dermatophagoides pteronyssinus* and *Dermatophagoides farinae* are reported as important sources of allergen in house dust [Allerg. Asthma, 10, 329–334 (1964); J. Allergy, 42, 14–28 (1968)]. From these mite species, major mite allergens were fractionally separated and identified as glycoproteins (pI 4.6 to 7.2) having a molecular weight of 24 to 28 kD and/or proteins (pI 5 to 7.2) having a molecular weight of 14.5 to 20 kD, both of which are contained in mite excretion and/or mite bodies [J. Immunol., 125, 587–592 (1980); J. Allergy Clin. Immunol., 76, 753–761 (1985); Immunol., 46, 679–687 (1982); Int. Arch. Allergy Appl. Immunol., 81, 214–223 (1986); J. Allergy Clin. Immunol., 75, 686–692 (1985) and other publications].

However, none of the existing antigens for hyposensitization therapy is effective and safe.

Mite allergen genes have been cloned; for example, with respect to Der p I (molecular weight: 25,371) and Der p II (molecular weight: 14,131 and 17,460), the major allergens of *Dermatophagoides pteronyssinus*, and Der f II (the molecular weight remains undetermined because the initiation codon remains unidentified), the major allergen of *Dermatophagoides farinae*, the gene of each major allergen was cloned and its nucleotide sequences were determined [Int. Arch. Allergy Appl. Immunol., 85, 127–129 (1988); J. Exp. Med., 167, 175–182 (1988); J. Exp. Med., 170, 1457–1462 (1989); Int. Arch. Allergy Appl. Immunol., 91, 118–123 (1990); Int. Arch. Allergy Appl. Immunol., 91, 124–129 (1990); Jpn. J. Allergol., 39, 557–561 (1990); Agric. Biol. Chem., 55, 1233–1238 (1991)], and attempts have been made to study mite allergens by genetic recombination technology.

However, none of the existing mite allergens can serve as a sensitized antigen.

On the other hand, the diagnosis of mite allergic diseases has been mostly based on inquiry in combination with skin reaction test using a house dust extract and/or mite body extract, with measurements of serum IgE antibody titer (relative value) taken by the RAST (radio allergosorbent test) method, an inhalation provocation test and a nasal mucosal provocation test conducted concurrently in only a few cases. It has therefore been very difficult to make direct diagnosis of mite allergic diseases.

It has been the traditional practice to use a house dust extract for hyposensitization therapy for bronchial asthma caused by house dust mites as a specific antigen. However, it is subject to extreme limitation with respect to dose and its therapeutic effect is very low, since its chemical composition is very indefinite and it contains a wide variety of impure substances which may induce anaphylaxis.

Thus, from the viewpoint of efficacy and safety, it is desired to develop a useful antigen for hyposensitization therapy, and it is also expected that such a high quality antigen for hyposensitization therapy will be supplied stably.

However, it is difficult to stably supply such a safe mite allergen in sufficient amounts to ensure the desired effect by a method based on extraction and purification of mite allergen from mite culture because this method lacks mass-productivity and is subject to quantitative limitation.

SUMMARY OF THE INVENTION

The present invention aims at overcoming these drawbacks by providing a recombinant mite allergen which is free of anaphylaxis-provoking impurities and which serves as a safe and effective therapeutic agent and diagnostic reagent for mite allergic diseases.

Accordingly, it is an object of the present invention to provide a recombinant mite allergen obtained by expression of a mite-body-derived gene.

It is another object of the invention to provide a gene which codes for said mite allergen.

It is still another object of the invention to provide a mite allergen fragment.

It is yet another object of the invention to provide a polypeptide having an epitope contained in mite allergen or a polypeptide having an epitope which can be regarded as immunologically identical to said epitope.

It is also another object of the invention to provide a gene which codes for the above-mentioned polypeptide having an epitope.

It is also another object of the invention to provide an expression vector capable of expressing the gene of the invention.

It is also another object of the invention to provide a transformant carrying an expression vector capable of expressing said gene.

It is also another object of the invention to provide a production method for said recombinant mite allergen.

It is also another object of the invention to provide a new therapeutic agent for mite allergic diseases whose active ingredient is the recombinant mite allergen of the invention.

It is also another object of the invention to provide a new diagnostic reagent for mite allergic diseases whose active ingredient is the recombinant mite allergen of the invention.

It is also another object of the invention to provide a new therapeutic agent for mite allergic diseases whose active ingredient is the mite allergen fragment of the invention.

It is also another object of the invention to provide a new diagnostic reagent for mite allergic diseases whose active ingredient is the mite allergen fragment of the invention.

It is also another object of the invention to provide a new therapeutic agent for mite allergic diseases whose active ingredient is the epitope-containing polypeptide of the invention.

It is also another object of the invention to provide a new diagnostic reagent for mite allergic diseases whose active ingredient is the epitope-containing polypeptide of the invention.

The present inventors made intensive investigations to solve the problems described above, and found a gene which coded for mite allergen possessing potent allergen activity from mite bodies. The inventors made further investigations based on this finding, and developed the present invention.

Accordingly, the present invention relates to:

(1) a recombinant mite allergen containing the partial amino acid sequence shown below (SEQ ID NO:1), obtainable by expression of a mite-body-derived gene, Phe Val Met Lys Arg Glu Pro Leu Arg Phe Arg Asp Ile Thr Val Glu Gly Asn Glu Asn Ala Tyr Ile Lys Asn Gly Lys Leu His Leu Ser Leu Met Asp Pro Ser Thr Leu Ser Leu Val Thr Lys Ala Asp Gly Lys Ile Asp Met Thr Val Asp Leu Ile Ser Pro Val Thr Lys Arg Ala Ser Leu Lys Ile Asp Ser Lys Lys Tyr Asn Leu Phe His Glu Gly Glu Leu Ser Ala Ser Ile (2) a recombinant mite allergen containing the partial amino acid sequence shown below (SEQ ID NO:2), obtainable by expression of a mite-body-derived gene, (3) a mite-body-derived gene which codes for an allergen active protein containing the amino acid sequence described in (1) or (2) above, (4) a mite allergen fragment containing at least an amino acid sequence encoded in the region of about 170 bp to about 270 bp, about 270 bp to about 400 bp, or about 170 bp to about 400 bp from the upstream in the nucleotide sequence shown in FIG. 10, (5) a polypeptide having an epitope contained in mite allergen or a polypeptide having an epitope which can be regarded as immunologically identical to said epitope, (6) a gene which codes for the polypeptide described in (5) above, (7) an expression vector capable of expressing the gene described in (3) or (5) above, (8) a bacterium, yeast or mammalian cell transformed with the expression vector described in (7) above, (9) a method for producing a recombinant mite allergen which comprises cultivating the bacterium, yeast or Phe Val Met Lys Arg Glu Pro Leu Arg Phe Arg Asp Ile Thr Val Glu Gly Asn Glu Asn Ala Tyr Ile Lys Asn Gly Lys Leu His Leu Ser Leu Met Asp Pro Ser Thr Leu Ser Leu Val Thr Lys Ala Asp Gly Lys Ile Asp Met Thr Val Asp Leu Ile Ser Pro Val Thr Lys Arg Ala Ser Leu Lys Ile Asp Ser Lys Lys Tyr Asn Leu Phe His Glu Gly Glu Leu Ser Ala Ser Ile Val Asn Pro Arg Leu Ser Trp His Gln Tyr Thr Lys Arg Asp Ser Arg Glu Tyr Lys Ser Asp Val Glu Leu Ser Leu Arg Ser Ser Asp Ile Ala Leu Lys Ile Thr Met Pro Asp Tyr Asn Ser Lys Ile His Tyr Ser Arg Gln Gly Asp Gln Ile Asn Met Asp Ile Asp Gly Thr Leu Ile Glu Gly His Ala Gln Gly Thr Ile Arg Glu Gly Lys Ile His Ile Lys Gly Arg Gln Thr Asp Phe Glu Ile Glu Ser Asn Tyr Arg Tyr Glu Asp Gly Lys Leu Ile Ile Glu Pro Val Lys Ser Glu Asn Gly Lys Leu Glu Gly Val Leu Ser Arg Lys Val Pro Ser His Leu Thr Leu Glu Thr Pro Arg Val Lys Met Asn Met Lys Tyr Asp Arg Tyr Ala Pro Val Lys Val Phe Lys Leu Asp Tyr Asp Gly Ile His Phe Glu Lys His Thr Asp Ile Glu Tyr Glu Pro Gly Val Arg Tyr Lys Ile Ile Gly Asn Gly Lys Leu Lys Asp Asp Gly Arg His Tyr Ser Ile Asp Val Gln Gly Ile Pro Arg Lys Ala Phe Asn Leu Asp Ala Asp Leu Met Asp Phe Lys Leu Lys Val Ser Lys Pro Glu Asp Ser Asn Lys Ala Gln Phe Ser Tyr Thr Phe Asn Glu Tyr Thr Glu Thr Glu Glu Tyr Glu Phe Asp Pro His Arg Ala Tyr Tyr Val Asn Trp Leu Ser Ser Ile Arg Lys Tyr Ile Gln Asn Phe Ile Val Glu Asp Asn mammalian cell described in (8) above under conditions which allow their gene to be expressed to produce a recombinant mite allergen and subsequently recovering said recombinant mite allergen,

(10) a pharmaceutical composition for the treatment of mite allergic diseases whose active ingredient is the recombinant mite allergen described in (1) or (2) above,

(11) a diagnostic reagent for mite allergic diseases whose active ingredient is the recombinant mite allergen described in (1) or (2) above,

(12) a pharmaceutical composition for the treatment of mite allergic diseases whose active ingredient is the mite allergen fragment described in (4) above,

(13) a diagnostic reagent for mite allergic diseases whose active ingredient is the mite allergen fragment described in (4) above,

(14) a pharmaceutical composition for the treatment of mite allergic diseases whose active ingredient is the polypeptide described in (5) above, and

(15) a diagnostic reagent for mite allergic diseases whose active ingredient is the polypeptide described in (5) above.

DETAILED DESCRIPTION OF THE INVENTION

Figure 1:
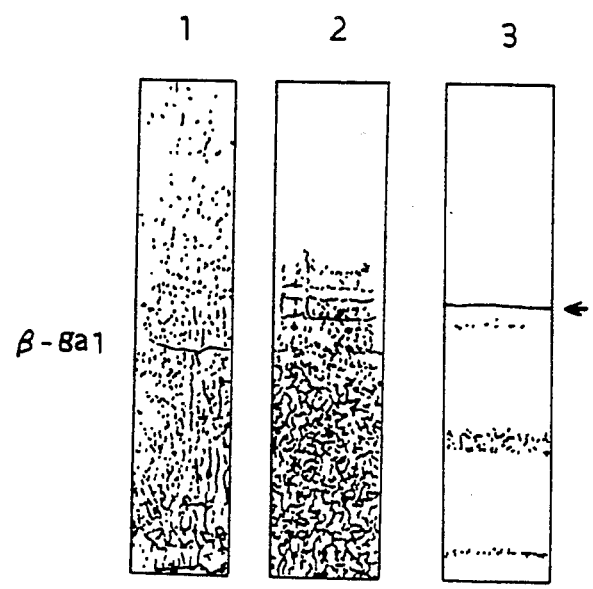
FIG. 1 shows the results of protein staining and immunological staining of the mite allergen fused protein expressed by λ gt11 inserting the mite allergen cDNA in the host E. coli Y1090 obtained after SDS-PAGE analysis followed by blot to a nitrocellulose membrane, in which lane 1 shows the results for a molecular marker (β-galactosidase, having a molecular weight of about 130000); lane 2 shows the results for the total protein of E. coli Y1090 cells; and lane 3 shows the results of immunological staining of the recombinant mite allergen (indicated with an arrow) using a rabbit anti-mite-body antigen serum.

The recombinant mite allergen of the present invention is obtained by expression of a mite-body-derived gene. Although the mite species used for the present invention are not subject to limitation, house dust mite species such as *Dermatophagoides farinae* and *Dermatophagoides pteronyssinus* are used.

The recombinant mite allergen of the present invention comprises a protein containing the partial amino acid sequence shown below (SEQ ID NO: 2) and possesses allergen activity.

| Phe | Val | Met | Lys | Arg | Glu | Pro | Leu | Arg | Phe | Arg | Asp | Ile | Thr | Val | Glu |
|-----|-----|-----|-----|-----|-----|-----|-----|-----|-----|-----|-----|-----|-----|-----|-----|
| Gly | Asn | Glu | Asn | Ala | Tyr | Ile | Lys | Asn | Gly | Lys | Leu | His | Leu | Ser | Leu |
| Met | Asp | Pro | Ser | Thr | Leu | Ser | Leu | Val | Thr | Lys | Ala | Asp | Gly | Lys | Ile |
| Asp | Met | Thr | Val | Asp | Leu | Ile | Ser | Pro | Val | Thr | Lys | Arg | Ala | Ser | Leu |
| Lys | Ile | Asp | Ser | Lys | Lys | Tyr | Asn | Leu | Phe | His | Glu | Gly | Glu | Leu | Ser |
| Ala | Ser | Ile | | | | | | | | | | | | | |

Another recombinant mite allergen of the present invention comprises a protein containing the amino acid sequence shown below (SEQ ID NO: 4), which contains the partial amino acid sequence shown above, and possesses allergen activity.

| Phe | Val | Met | Lys | Arg | Glu | Pro | Leu | Arg | Phe | Arg | Asp | Ile | Thr | Val | Glu |
|-----|-----|-----|-----|-----|-----|-----|-----|-----|-----|-----|-----|-----|-----|-----|-----|
| Gly | Asn | Glu | Asn | Ala | Tyr | Ile | Lys | Asn | Gly | Lys | Leu | His | Leu | Ser | Leu |
| Met | Asp | Pro | Ser | Thr | Leu | Ser | Leu | Val | Thr | Lys | Ala | Asp | Gly | Lys | Ile |
| Asp | Met | Thr | Val | Asp | Leu | Ile | Ser | Pro | Val | Thr | Lys | Arg | Ala | Ser | Leu |
| Lys | Ile | Asp | Ser | Lys | Lys | Tyr | Asn | Leu | Phe | His | Glu | Gly | Glu | Leu | Ser |
| Ala | Ser | Ile | Val | Asn | Pro | Arg | Leu | Ser | Trp | His | Gln | Tyr | Thr | Lys | Arg |

-continued

Asp Ser Arg Glu Tyr Lys Ser Asp Val Glu Leu Ser Leu Arg Ser Ser

Asp Ile Ala Leu Lys Ile Thr Met Pro Asp Tyr Asn Ser Lys Ile His

Tyr Ser Arg Gln Gly Asp Gln Ile Asn Met Asp Ile Asp Gly Thr Leu

Ile Glu Gly His Ala Gln Gly Thr Ile Arg Glu Gly Lys Ile His Ile

Lys Gly Arg Gln Thr Asp Phe Glu Ile Glu Ser Asn Tyr Arg Tyr Glu

Asp Gly Lys Leu Ile Ile Glu Pro Val Lys Ser Glu Asn Gly Lys Leu

Glu Gly Val Leu Ser Arg Lys Val Pro Ser His Leu Thr Leu Glu Thr

Pro Arg Val Lys Met Asn Met Lys Tyr Asp Arg Tyr Ala Pro Val Lys

Val Phe Lys Leu Asp Tyr Asp Gly Ile His Phe Glu Lys His Thr Asp

Ile Glu Tyr Glu Pro Gly Val Arg Tyr Lys Ile Ile Gly Asn Gly Lys

Leu Lys Asp Asp Gly Arg His Tyr Ser Ile Asp Val Gln Gly Ile Pro

Arg Lys Ala Phe Asn Leu Asp Ala Asp Leu Met Asp Phe Lys Leu Lys

Val Ser Lys Pro Glu Asp Ser Asn Lys Ala Gln Phe Ser Tyr Thr Phe

Asn Glu Tyr Thr Glu Thr Glu Glu Tyr Glu Phe Asp Pro His Arg Ala

Tyr Tyr Val Asn Trp Leu Ser Ser Ile Arg Lys Tyr Ile Gln Asn Phe

Ile Val Glu Asp Asn

The recombinant mite allergen of the present invention may be any variant resulting from the substitution, deletion, addition or translocation of one or more amino acids in the amino acid sequence shown above, as long as it possesses allergen activity. Such a variant can be obtained as a naturally-occurring allelic variant or by inducing mutation at a specific site of DNA by recombinant DNA technology.

The recombinant mite allergen of the present invention may be expressed as a fused protein with another protein. In the present specification, a recombinant mite allergen expressed in a fusion with another protein is also referred to as a fused recombinant mite allergen in some cases. Although the other protein involved in the fusion is not subject to limitation, examples thereof include β-galactosidase, glutathione-S-transferase and protein A.

The recombinant mite allergen of the present invention may be a protein fragment comprising only a region essential to allergen activity, and may comprise a domain essential to allergen activity.

In the present specification, an active fragment possessing allergen activity is referred to as a mite allergen fragment. Examples thereof include fragments containing at least an amino acid sequence encoded in the region of about 170 bp to about 270 bp, about 270 bp to about 400 bp, or about 170 bp to 400 bp from the translation start in the restriction map shown in FIG. 10.

The recombinant mite allergen of the present invention may be obtained not only by expressing mite allergen protein alone but also by eliminating the other protein from a fused protein.

In short, the recombinant mite allergen of the present invention is an allergen active protein which substantially contains the above-mentioned amino acid sequence obtained by expression of a mite-body-derived gene.

The recombinant mite allergen of the present invention is exemplified by the following β-galactosidase-fused recombinant mite allergen expressed in E. coli. The fused recombinant mite allergen expressed in E. coli is purified by gel filtration chromatography using Ultrogel AcA 44 (produced by LKB), anti-β-galactosidase antibody immobilized affinity chromatography and anti-mite-body antibody immobilized affinity chromatography, and possesses the following properties as a recombinant mite allergen.

1) Color and appearance: White.
2) Water solubility: Freely soluble.
3) Molecular weight: About 40000, as estimated by SDS-PAGE using the equation given below.

Molecular weight of fused protein-molecular weight of β-galactosidase

4) Contains the partial amino acid sequence shown below (SEQ ID NO:2),

Phe Val Met Lys Arg Glu Pro Leu Arg Phe Arg Asp Ile Thr Val Glu

Gly Asn Glu Asn Ala Tyr Ile Lys Asn Gly Lys Leu His Leu Ser Leu

Met Asp Pro Ser Thr Leu Ser Leu Val Thr Lys Ala Asp Gly Lys Ile

Asp Met Thr Val Asp Leu Ile Ser Pro Val Thr Lys Arg Ala Ser Leu

Lys Ile Asp Ser Lys Lys Tyr Asn Leu Phe His Glu Gly Glu Leu Ser

Ala Ser Ile or contains the amino acid sequence shown below (SEQ ID NO:4), which contains the partial amino acid sequence shown above (SEQ ID NO:1).

tein by a conventional method and observed for anaphylaxis reaction upon booster immunization.

The mite-body-derived gene of the present invention

Phe Val Met Lys Arg Glu Pro Leu Arg Phe Arg Asp Ile Thr Val Glu
Gly Asn Glu Asn Ala Tyr Ile Lys Asn Gly Lys Leu His Leu Ser Leu
Met Asp Pro Ser Thr Leu Ser Leu Val Thr Lys Ala Asp Gly Lys Ile
Asp Met Thr Val Asp Leu Ile Ser Pro Val Thr Lys Arg Ala Ser Leu
Lys Ile Asp Ser Lys Lys Tyr Asn Leu Phe His Glu Gly Glu Leu Ser
Ala Ser Ile Val Asn Pro Arg Leu Ser Trp His Gln Tyr Thr Lys Arg
Asp Ser Arg Glu Tyr Lys Ser Asp Val Glu Leu Ser Leu Arg Ser Ser
Asp Ile Ala Leu Lys Ile Thr Met Pro Asp Tyr Asn Ser Lys Ile His
Tyr Ser Arg Gln Gly Asp Gln Ile Asn Met Asp Ile Asp Gly Thr Leu
Ile Glu Gly His Ala Gln Gly Thr Ile Arg Glu Gly Lys Ile His Ile
Lys Gly Arg Gln Thr Asp Phe Glu Ile Glu Ser Asn Tyr Arg Tyr Glu
Asp Gly Lys Leu Ile Ile Glu Pro Val Lys Ser Glu Asn Gly Lys Leu
Glu Gly Val Leu Ser Arg Lys Val Pro Ser His Leu Thr Leu Glu Thr
Pro Arg Val Lys Met Asn Met Lys Tyr Asp Arg Tyr Ala Pro Val Lys
Val Phe Lys Leu Asp Tyr Asp Gly Ile His Phe Glu Lys His Thr Asp
Ile Glu Tyr Glu Pro Gly Val Arg Tyr Lys Ile Ile Gly Asn Gly Lys
Leu Lys Asp Asp Gly Arg His Tyr Ser Ile Asp Val Gln Gly Ile Pro
Arg Lys Ala Phe Asn Leu Asp Ala Asp Leu Met Asp Phe Lys Leu Lys
Val Ser Lys Pro Glu Asp Ser Asn Lys Ala Gln Phe Ser Tyr Thr Phe
Asn Glu Tyr Thr Glu Thr Glu Glu Tyr Glu Phe Asp Pro His Arg Ala
Tyr Tyr Val Asn Trp Leu Ser Ser Ile Arg Lys Tyr Ile Gln Asn Phe
Ile Val Glu Asp Asn

5) Possesses antigenicity. Judged on the basis of the ELISA reactivity with the specific IgG in mite allergy patient's pool serum, rabbit anti-mite-body serum and rabbit anti-β-galactosidase, and the reactivity with the above-mentioned antiserum after SDS-PAGE of the expressed protein followed by blot to a nitrocellulose membrane.

6) Possesses allergen activity. Judged by a histamine release test of a mite allergy patient leukocyte based on high performance liquid chromatography.

7) Does not induce anaphylaxis reaction. Guinea pigs are immunized with fused protein or mite allergen prois obtained by preparing the mRNA from live mite bodies and synthesizing the cDNA by a conventional method using said mRNA as a template. It codes for an allergen-active protein containing the amino acid sequence described above in the molecule. Examples of the DNA which codes for the partial amino acid sequence include the sequence shown below (SEQ ID NO:2).

```
TTT GTC ATG AAA CGA GAA CCA TTG CGA TTC AGA GAC ATC ACT GTC GAA
GGA AAC GAA AAT GCC TAT ATC AAA AAT GGC AAA CTT CAT TTG TCG CTT
ATG GAT CCG TCA ACA TTG AGT TTA GTC ACG AAA GCC GAT GGA AAA ATC
GAC ATG ACA GTA GAC TTG ATA TCG CCA GTC ACA AAA CGT GCA TCG TTG
AAA ATT GAT TCA AAG AAA TAC AAC CTT TTC CAT GAA GGT GAA TTG AGT
GCA TCG ATC
```

The DNA is also exemplified by the nucleotide sequence shown below (SEQ ID NO:4), which contains the nucleotide sequence shown above.

```
TTT GTC ATG AAA CGA GAA CCA TTG CGA TTC AGA GAC ATC ACT GTC GAA
GGA AAC GAA AAT GCC TAT ATC AAA AAT GGC AAA CTT CAT TTG TCG CTT
ATG GAT CCG TCA ACA TTG AGT TTA GTC ACG AAA GCC GAT GGA AAA ATC
```

-continued

```
GAC ATG ACA GTA GAC TTG ATA TCG CCA GTC ACA AAA CGT GCA TCG TTG

AAA ATT GAT TCA AAG AAA TAC AAC CTT TTC CAT GAA GGT GAA TTG AGT

GCA TCG ATC GTA AAC CCA CGA TTG TCA TGG CAT CAA TAC ACG AAA CGC

GAT TCT CGT GAA TAC AAG AGT GAT GTA GAA CTA TCG TTG CGA TCG TCG

GAC ATT GCT CTC AAG ATT ACG ATG CCT GAT TAT AAT TCG AAA ATT CAT

TAT TCA CGA CAA GGT GAT CAA ATC AAC ATG GAC ATC GAT GGT ACA TTG

ATC GAA GGT CAT GCA CAA GGA ACC ATC AGA GAA GGT AAA ATC CAC ATT

AAA GGT AGA CAA ACT GAT TTC GAG ATC GAA TCC AAC TAC CGA TAC GAA

GAT GGC AAA CTA ATC ATC GAA CCG GTC AAG AGT GAA AAT GGC AAA TTG

GAA GGC GTT CTT TCC CGT AAG GTG CCA TCA CAT CTG ACA CTA GAA ACA

CCA CGA GTC AAG ATG AAT ATG AAA TAT GAT CGA TAT GCA CCA GTC AAA

GTG TTC AAA TTG GAT TAT GAT GGC ATC CAC TTC GAG AAA CAT AAC GAT

ATT GAA TAC GAA CCT GGC GTT CGA TAC AAG ATC ATC GGC AAT GGA AAA

CTC AAG GAT GAT GGC CGC CAC TAT TCT ATC GAT GTG CAA GGT ATT CCA

CGC AAA GCA TTC AAT CTG GAC GCT GAC TTG ATG GAT TTC AAA CTG AAA

GTG AGC AAG CCA GAA GAT AGC AAT AAA GCT CAA TTC AGC TAC ACA TTC

AAC GAA TAT ACC GAG ACC GAA GAA TAT GAA TTC GAT CCA CAT CGT GCC

TAT TAT GTT AAT TGG TTG AGT TCC ATT CGC AAA TAC ATC CAG AAT TTC

ATC GTC GAA GAC AAC
```

This DNA sequence is not homologous to any of the DNA sequences reported for the allergens Der p I, Der p II and Der f II.

Figure 4:
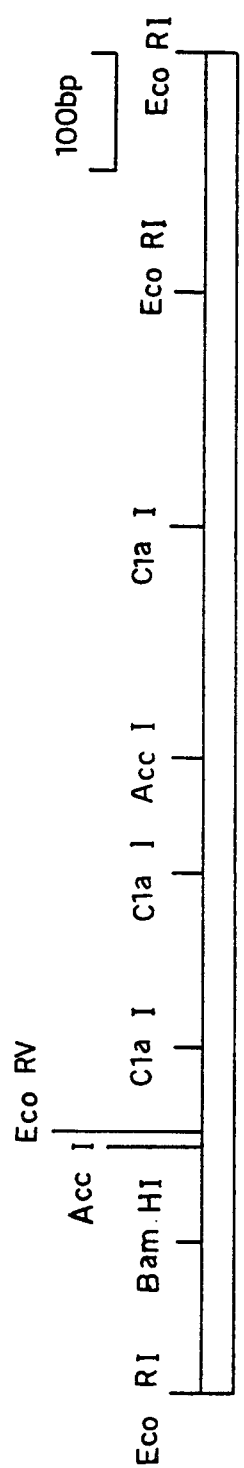
FIG. 4 is the restriction enzyme map of the cDNA which codes for mite allergen.

With respect to the mite-body-derived gene of the present invention, the total nucleotide chain length of the cDNA is about 1.2 kbp [determined by agarose electrophoresis, the length is 1143 bp (about 1.1 kbp) when the linker is excluded, but the length of the translated base chain is 1026 bp (about 1 kbp), including the termination codon, since expression completes at the termination codon before the linker in actual expression], and it has the restriction enzyme map shown in FIG. 4.

The expression vector of the present invention is bound so that the gene of the present invention described above is expressed in a transformed bacterium, yeast or mammalian cell. The vector DNA used to construct the expression vector is not subject to limitation; any widely available vector DNA can be used, including pUC18, pTV118N (produced by Takara Shuzo), pUEX2 (produced by Amersham), pKK233-2 (produced by Pharmacia) and pMAM-neo (produced by Clontech).

pAK1, an expression vector of the present invention, can be obtained by, for example, digesting the mite allergen cDNA inserted in λgt11 phage with Kpn I-Sac I and ligating to the plasmid vector pUC18 at the Kpn I-Sac I site. Another expression vector pAKE1 can be obtained by ligating the EcoR I digestion fragment of pAK1 to pUC18 at the EcoR I site in the same manner as above. A still another expression vector pAEX201 can be obtained by ligating the EcoR I digestion fragment of pAKE1 to pUEX2 (produced by Amersham) previously cleaved by EcoR I digestion.

The bacterium, yeast or mammalian cell transformed with the expression vector of the present invention is not subject to limitation, as long as it is capable of expressing the gene of the invention. Examples of such bacteria include E. coli and Bacillus subtilis. Examples of such yeasts include Saccharomyces cereviceae. Examples of such mammalian cells include Chinese hamster ovary (CHO) cells, simian COS cells and mouse fibroblasts.

The method for production of recombinant mite allergen of the present invention comprises cultivating a bacterium, yeast or mammalian cell transformed with an expression vector which permits the expression of the gene of the present invention under conditions which permit the expression of said gene to produce recombinant mite allergen and then recovering said recombinant mite allergen.

The method for production of recombinant mite allergen using an E. coli transformant carrying a fused protein expression plasmid inserting the mite allergen cDNA is exemplified as follows:

First, an E. coli transformant carrying a β-galactosidase-fused protein expression plasmid inserting the mite allergen cDNA is subjected to shaking culture by a conventional method to the logarithmic phase, and fused protein is inductively synthesized by making a temperature shift or adding a β-galactosidase inducer while maintaining this logarithmic phase. Examples of E. coli strains used as host cells include E. coli pop2136 (produced by Amersham), and the strain transformed with expression vector is named E. coli pop2136 OL-1 (FERM BP-3497).

After completion of the cultivation, cells are harvested, suspended in a buffer containing serine, cysteine, aspartic acid and metallic protease inhibitors and disrupted by ultrasonication. The membrane-localized protein in the cell debris is extracted with a buffer containing both protease inhibitors such as phenylmethanesulfonyl fluoride, monoiodoacetic acid, pepstatin A and ethylenediaminetetraacetic acid and a detergent such as sodium lauryl sulfate (SDS), Triton X-100 or Nonidet P40. The mite allergen-β-galactosidase fused protein obtained from the extract or culture concentrate is purified by, for example, gel filtration chromatography using Ultrogel AcA 44 (produced by LKB), anti-β-galactosidase antibody immobilized affinity chromatography and anti-mite-body antibody im mobilized affinity chromatography. The anti-β-galactosidase antibody immobilized carrier is prepared by covalently binding an anti-β-galactosidase antibody (produced by 5Prime→3Prime Inc.) to an activated tresyl carrier such as tresyl GM gel (produced by Kurita Water Industries Ltd.), tresyl Toyopearl (produced by Tosoh Corporation) or tresyl Sepharose (produced by Pharmacia). The anti-mite-body antibody immobilized carrier is prepared by covalently binding a rabbit anti-mite-body antibody to the above-mentioned activated carrier.

The purified recombinant mite allergen fused protein is digested with protease and then fractionated by one or more of the known purification methods such as gel filtration chromatography, ultrafiltration, ion exchange chromatography, affinity chromatography, hydrophobic chromatography, chromatofocusing, isoelectric focusing and gel electrophoresis, while monitoring the course of fractionation by ELISA and a mite allergy patient leukocyte histamine release test [Arerugi, 37, 725 (1988)]. From the active fraction thus obtained, the protein components originating from β-galactosidase are absorbed and removed through an anti-β-galactosidase antibody immobilized affinity column, after which the recombinant mite allergen fragment is purified using an anti-mite-body antibody immobilized affinity column.

The above-mentioned methods can also be used singly or in combination to purify the mite allergen fragment from the digested product of the fused protein purified by the method described above with a protease such as pronase, subtilisin, thermolisine or trypsin, or from the decomposition product obtained by treatment with a chemical such as cyanogen bromide, 2-nitro-5-thiocyanobenzoic acid or hydroxylamine.

The production method for recombinant mite allergen of the present invention includes not only direct expression of mite allergen protein but also the method in which a fused protein expressed as a fused recombinant mite allergen resulting from fusion of mite allergen with another protein via an intervening sequence is recovered and subsequently the fused other protein is eliminated.

Examples of the other protein to be fused include β-galactosidase, glutathione-S-transferase, protein A and other proteins which are generally known to form a fused protein.

Elimination of the other protein can also be achieved by a known method. For example, when the other protein is β-galactosidase and a part of collagen or fibrinogen protein is present between the other protein and the mite allergen protein, the mite allergen protein is purified by one or more of the methods described above using collagenase or thrombin to leave the fusion protein.

The mite allergen fragment of the present invention can easily be obtained as a recombinant mite allergen by constructing an expression vector from the DNA which codes for the amino acid sequence of said fragment by a conventional method and expressing the DNA in an appropriate host.

Moreover, said mite allergen fragment can be used as a synthetic mite allergen, synthesized by the conventional solid phase synthesis method, singly or in conjugation with an appropriate carrier such as human serum albumin or sea squirt antigen, which has been confirmed as safe in intracutaneous administration.

Examples of the polypeptide of the present invention, which has an epitope contained in the mite allergen derived from mite body, or the polypeptide having an epitope which can be regarded as immunologically identical to said epitope, include the polypeptides having the amino acid sequence shown below (SEQ ID NO: 6), Met Thr Val Asp Leu Ile Ser Pro Val Thr Lys Arg Ala Ser Leu Lys Ile Asp Ser Lys Lys Tyr or the amino acid sequence shown below (SEQ ID NO: 8).

Asp Val Glu Leu Ser Leu Arg Ser Ser Asp Ile Ala

Examples of the gene which codes for these polypeptides include those containing the DNA sequence shown below (SEQ ID NO: 6),

ATG ACA GTA GAC TTG ATA TCG CCA GTC ACA AAA CGT GCA TCG TTG AAA

ATT GAT TCA AAG AAA TAC or the DNA sequence shown below (SEQ ID NO:8).

GAT GTA GAA CTA TCG TTG CGA TCG TCG GAC ATT GCT

The polypeptide of the present invention, which has an epitope contained in the mite allergen derived from mite body, or the polypeptide having an epitope which can be regarded as immunologically identical to said epitope, is exemplified above. Although both of them can be used as an active ingredient of a pharmaceutical composition for mite allergic diseases or diagnostic reagent for mite allergic diseases, the polypeptide of SEQ ID NO:8 is preferably used since it is more highly antigenic.

The pharmaceutical composition for the treatment of mite allergic diseases of the present invention contains as an active ingredient the purified recombinant mite allergen, mite allergen fragment or epitope-containing polypeptide described above, and is used to treat various mite allergic diseases. Here, mite allergic diseases include all allergic diseases caused by the specific antigen of mites, such as atopic bronchial asthma, allergic rhinitis, allergic conjunctivitis and allergic dermatitis.

The pharmaceutical composition for the treatment of mite allergic diseases of the present invention is not subject to limitation with respect to the method of its preparation. For example, the recombinant mite allergen purified by the method described above or the mite allergen fragment or epitope-containing polypeptide purified in accordance with the methods described above is dried and collected in a powder form and used as a hyposensitization therapeutic agent for mite allergic diseases. In hyposensitization therapy, the pharmaceutical composition for mite allergic diseases of the present invention may be used as such or in the form of a formula preparation prepared by adding as necessary a commonly used adjuvant or various additives such as a stabilizer, excipient, dissolution aid, emulsifier, buffer, soothing agent, preservative and colorant by a conventional method. For example, recombinant mite allergen purified in a powder form is dissolved in a phenol-containing saline, and this solution is used as a stock solution of an antigen for hyposensitization therapy.

The pharmaceutical composition of the present invention thus obtained comprises as the active ingredient a pharmaceutically effective amount of the recombinant mite allergen and at least one pharmaceutically acceptable carrier or diluent.

The pharmaceutical composition for mite allergic diseases of the present invention can be administered by ordinary routes such as peroral, intracutaneous, subcutaneous, intramuscular and intraperitoneal injection. Moreover, it can be used as percutaneous or permucosal drugs such as troches, sublingual tablets, eye drops, intranasal spray, poultices, creams and lotions.

As for the dosage and administration frequency of the pharmaceutical composition for mite allergic diseases of the present invention, they are appropriately selected according to the route of administration, symptoms and other conditions so that the dosage does not exceed about 20 $\mu$g per administration for an adult, with an administration frequency of about one time weekly.

The pharmaceutical composition for mite allergic diseases of the present invention is useful not only as a therapeutic agent but also as a preventive agent for mite allergic diseases. Since the pharmaceutical composition for mite allergic diseases of the present invention is free from anaphylaxis inductive action, it can be safely used for humans.

The diagnostic reagent for mite allergic diseases of the present invention is used as a skin reaction diagnostic reagent for mite allergic diseases and as a titrating reagent for the diagnosis of mite allergy.

When used as a skin reaction diagnostic reagent, the diagnostic reagent for mite allergic diseases of the present invention is prepared by a conventional method from the recombinant mite allergen purified by the methods described above or the mite allergen fragment or epitope-containing polypeptide purified in accordance with the methods described above. For example, the recombinant mite allergen is dried to a powder form, which is dissolved in a phenol-containing saline and used in dilution. The use as a skin reaction diagnostic reagent is in accordance with a conventional method.

Similarly, when used as a titrating reagent for the diagnosis of mite allergy, the diagnostic reagent for mite allergy diseases is prepared by a conventional method. For example, the recombinant mite allergen is appropriately dissolved in Hanks' solution and used after dilution as a reagent for histamine release titration. This method is carried out normally by the following procedure.

Blood of a mite allergy patient and a blood cell fraction obtained from this blood by centrifugation are suspended in a buffer to yield a blood cell suspension. A given amount of this suspension is titrated using the recombinant mite allergen, a titrating reagent, and the amount of histamine released from basophiles (a kind of leukocyte) in response to allergen stimulation is determined by HPLC [Arerugi, 37, 725 (1988)].

In this histamine release titration, the amount of histamine released is calculated from the 50% level (inflexion point of the titration curve) of the maximum release. This titration has two features. (1) The patient's allergen sensitivity is measured directly from the titer of the blood cell suspension. (2) After pre-reacting blood plasma and recombinant mite allergen, the value obtained by titrating the blood cell suspension with the reaction solution (blood titration curve value) is usually higher than the value obtained by titrating the blood cell suspension with the recombinant mite allergen (blood cell suspension titration curve value). This is because the blood plasma contains an IgG antibody (blocking antibody) capable of allergen neutralization.

Therefore, the blocking antibody titer can be obtained from the degree of shift of the blood titration curve from the blood cell suspension titration curve. On the basis of the allergen sensitivity and this blocking antibody titer, accurate diagnosis of mite allergy is feasible. This histamine release titration test is useful to monitor the effect of hyposensitization therapy.

EXAMPLES

The present invention is hereinafter described in more detail by means of the following examples, but the invention is not limited by these examples.

EXAMPLE 1

Extraction of total mite RNA 6 g of live mite bodies obtained by cultivating *Dermatophagoides farinae* by a conventional method, together with 10 g of quartz sand, in 200 ml of a solution of 5.5M guanidine isocyanate (produced by Katayama Kagaku), was ground in a mortar and centrifuged. The resulting supernatant was repeatedly taken in and out with a 50-ml syringe equipped with an 18G injection needle to partially cleave the DNA. After additional centrifugation, the supernatant was layered on a solution of caesium trifluoroacetate (produced by Katayama Kagaku) in a ratio of 16 ml of the former to 17 ml of the latter and subjected to density gradient centrifugation at 85000× g for 24° C. (15° C., HITACHI SCP55H swing PRS-27-2), and the total RNA fraction forming a pellet on the tube bottom was recovered.

This total RNA fraction was dissolved in a solution of 4.0M guanidine isocyanate and precipitated with ethanol to yield 1 ml of a solution of TE (10 mM Tris-HCl, pH 7.5, 1 mM EDTA).

EXAMPLE 2

Separation of mite allergen Poly(A) mRNA

The TE solution of this total mite RNA was heated at 65° C. for 10 minutes and rapidly cooled, after which an equal amount of 1M NaCl was added thereto, and the mixture was applied to an oligo (dT) cellulose column (column volume 0.5 ml, produced by Boehringer Mannheim) pre-equilibrated with a solution of STE (10 mM Tris-HCl, pH 7.5, 1 mM EDTA, 0.5M NaCl). After the effluent was recycled to the column, the column was washed with a 2.5-fold volume of STE solution. After column washing, poly(A) mRNA was eluted with TE solution. Here, 0.2 ml fractions were taken, and the fractions found to contain RNA by an ethidium bromide spot test were pooled. This column purification was conducted again, and the RNA was recovered by ethanol precipitation from the pooled fraction to yield a poly(A) mRNA fraction. The yield was determined to be about 20 µg in a spot test together with known concentrations of serial dilutions of the RNA solution.

EXAMPLE 3

Synthesis of mite allergen cDNA

Next, in the presence of 5 µg of the poly(A) mRNA as a template, a cDNA having a 13 mer linker at both ends and containing an EcoR I site was synthesized using a cDNA synthesis kit (produced by Pharmacia) in accordance with the instruction manual.

EXAMPLE 4

Preparation of mite allergen cDNA library

A one-fifth amount of the cDNA was mixed with 1 µg of EcoR I-digested λ gt11 (produced by Stratagene Cloning System). After concentration with ethanol, this mixture was reacted with 200 units of T4 DNA ligase at 12° C. for 15 hours, whereby the cDNA was inserted into λ gt11 at the EcoR I site. From this reaction mixture, a cDNA library was prepared using an in vitro packaging kit (Giga pack PLUS, produced by Stratagene Cloning System) in accordance with the instruction manual. After two cycles of this library preparation procedure, a total of 41000 pfu (plaque forming unit) of cDNA was prepared from 2 µg of poly(A) mRNA.

EXAMPLE 5

Cloning of mite allergen cDNA

The cDNA-inserted λ gt11 phage was suspended in a solution of SM (1M Tris-HCl, pH 7.5, 0.1M NaCl, 10 mM MgSO$_4$, 2% gelatin). This suspension, together with overnight-incubated E. coli Y1090 (produced by Stratagene Cloning System), was subjected to shaking culture at 37° C. for 30 minutes to infect the host with the phage. The resulting culture was spread over plates of LB agar medium [1% Bacto tryptone, 0.5% Bacto yeast extract, 1.5% Bacto agar (all produced by Difco Laboratories), 0.5% NaCl] so that about 2000 plaques per plate were formed. After cultivation at 42° C. for 3 hours, the medium was covered with a nitrocellulose membrane (Hibond-C, produced by Amersham) previously dried after immersing in 10 mM isopropyl-1-thio-β-D-galactoside (IPTG), followed by additional cultivation at 37° C. for 3 hours and transfer of the inductively synthesized β-galactosidase-fused protein onto the nitrocellulose membrane. After blocking for overnight in a TBS solution (10 mM Tris-HCl, pH 8.0, 0.9% NaCl) containing 2% BSA, the nitrocellulose membrane was reacted with a rabbit anti-mite-body antigen serum (100-fold dilution in TBS) for 1 hour and then with a peroxidase-coupled goat anti-rabbit IgG antibody (produced by Cappel, 2000-fold dilution in TBS) for 1 hour, and spots were visualized in a TBS solution containing 0.4 mg/ml diaminobenzidine tetrahydrochloride in the presence of 0.01% hydrogen peroxide.

The rabbit anti-mite-body antigen serum was obtained by suspending mite bodies from a whole mite culture with saturated saline and PBS, washing the mite bodies with PBS, grinding them and using the ground product as an immunogen for booster immunization of rabbits once weekly for 10 weeks. The plaque which corresponded to the position of the brown spot was picked up, suspended in SM and stored as a positive clone.

EXAMPLE 6

Expression of fused protein using λ gt11 phage vector

The positive clone obtained by immunological screening in Example 5, together with 50 µg of an overnight culture broth of E. coli Y1090, was subjected to shaking culture in 3 ml of an LB liquid medium containing 100 µg of 100 mM IPTG at 37° C. for 8 hours, and the resulting culture supernatant was dialyzed against distilled water and lyophilized to yield a sample for western blot.

SDS-PAGE was carried out in accordance with the method of Laemmli et al. [Nature, 227, 680-685 (1970)]. A 2 mg sample was electrophoresed under conditions of a polyacrylamide gel concentration of 5% and a constant electric current of 15 mA. Then, the sample was transferred from the acrylamide gel to Immobilon membrane (pore size 0.45 µm, produced by MILLIPORE) by electrophoresis in an SDS-running buffer (192 mM glycine-25 mM Tris, pH 8.3, 0.1% SDS, 20% methanol) at 8 to 10 V/cm for 2 hours. This Immobilon membrane was subjected to protein staining with Auro Dye (produced by JANSSEN Life Sciences Products) and immunological staining with a pool serum of a mite allergy patient, rabbit anti-mite-body antigen serum and rabbit anti-β-galactosidase antibody (produced by 5 Prime →3 Prime Inc.), and the mite allergen fused protein was detected (FIG. 1).

EXAMPLE 7

Construction of recombinant plasmid

Figure 2:
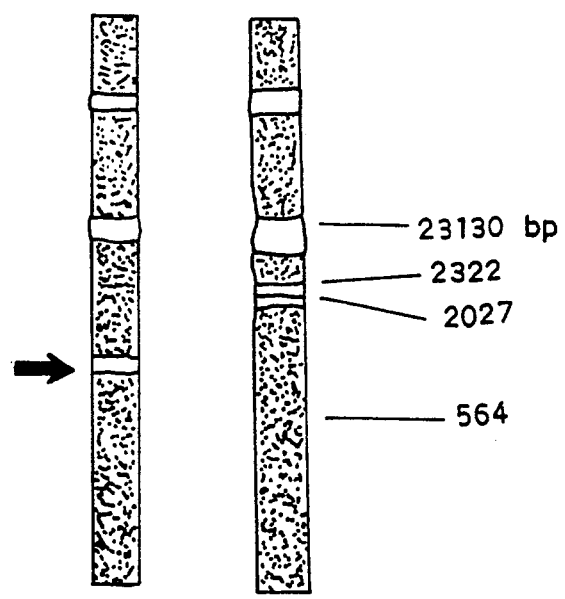
FIG. 2 shows the results of agarose electrophoresis of the cDNA which codes for mite allergen.
Figure 3:
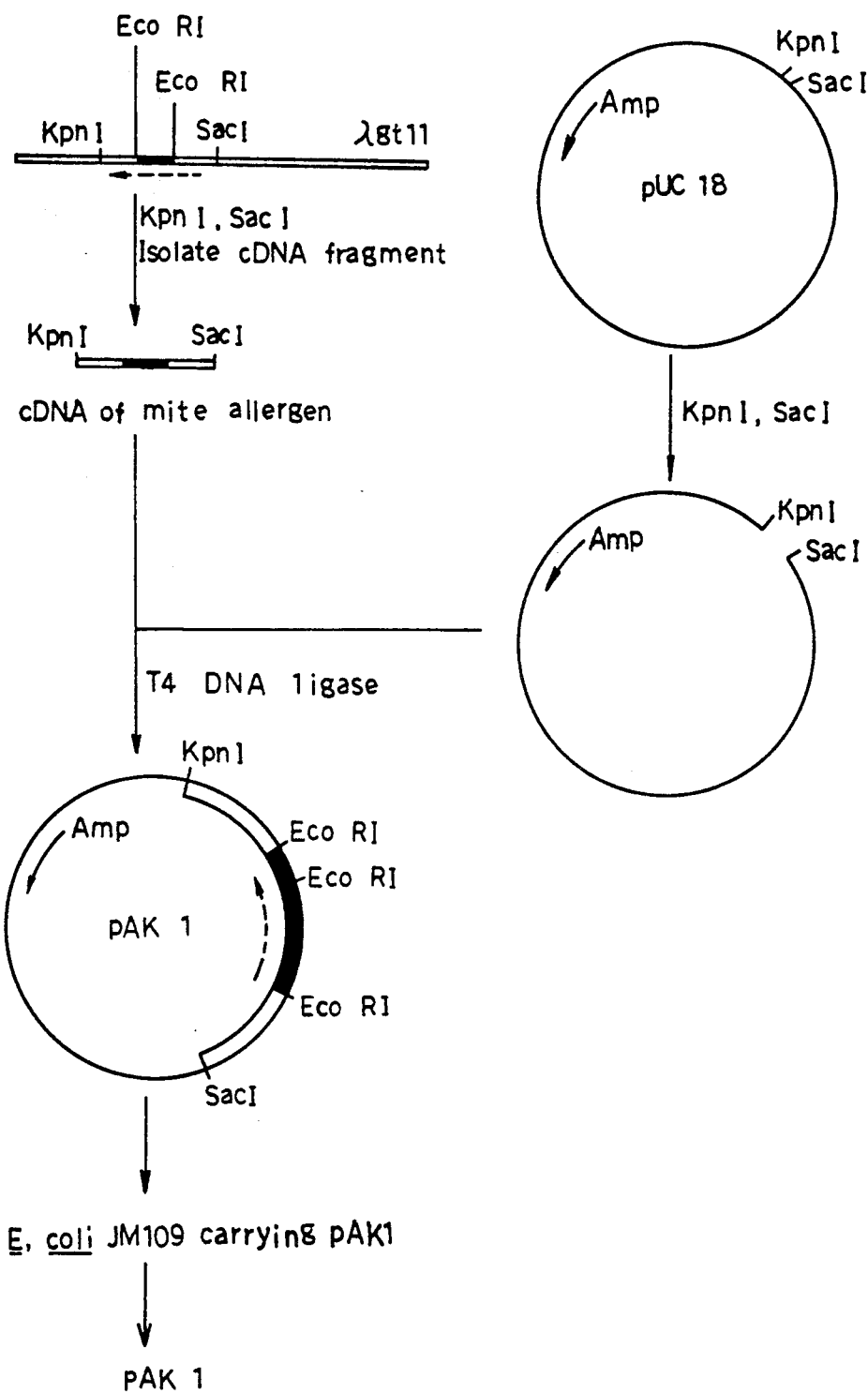
FIG. 3 shows the construction of the recombinant plasmid pAK1.

After recovery from the λ gt11 phage clone inserting the cDNA which codes for the mite allergen-β-galactosidase fused protein which reacted with these antisera, the DNA was digested with EcoR I. This digestion product was subjected to agarose gel electrophoresis, and the cDNA chain length was determined to be about 1.2 kbp (including the linker) (indicated by arrow in FIG. 2). Next, the λ gt11 phage DNA inserted this cDNA was digested with Kpn I-Sac I. The obtained fragment (about 3.3 kbp) was ligated to the plasmid vector pUC18 (produced by Takara Shuzo) at the Kpn I-Sac I site and transformed into E. coli JM109 (produced by Takara Shuzo) in accordance with the method of Hanahan [DNA Cloning, vol. 1, Glover, D. M. ed., pp. 109-136, IRL Press (1985)] (FIG. 3).

The obtained recombinant plasmid was named pAK 1, which was used to draw a restriction enzyme map (1144 bp, not including the linker) (FIG. 4).

EXAMPLE 8

Determination of nucleotide sequence of mite allergen cDNA

Figure 5:
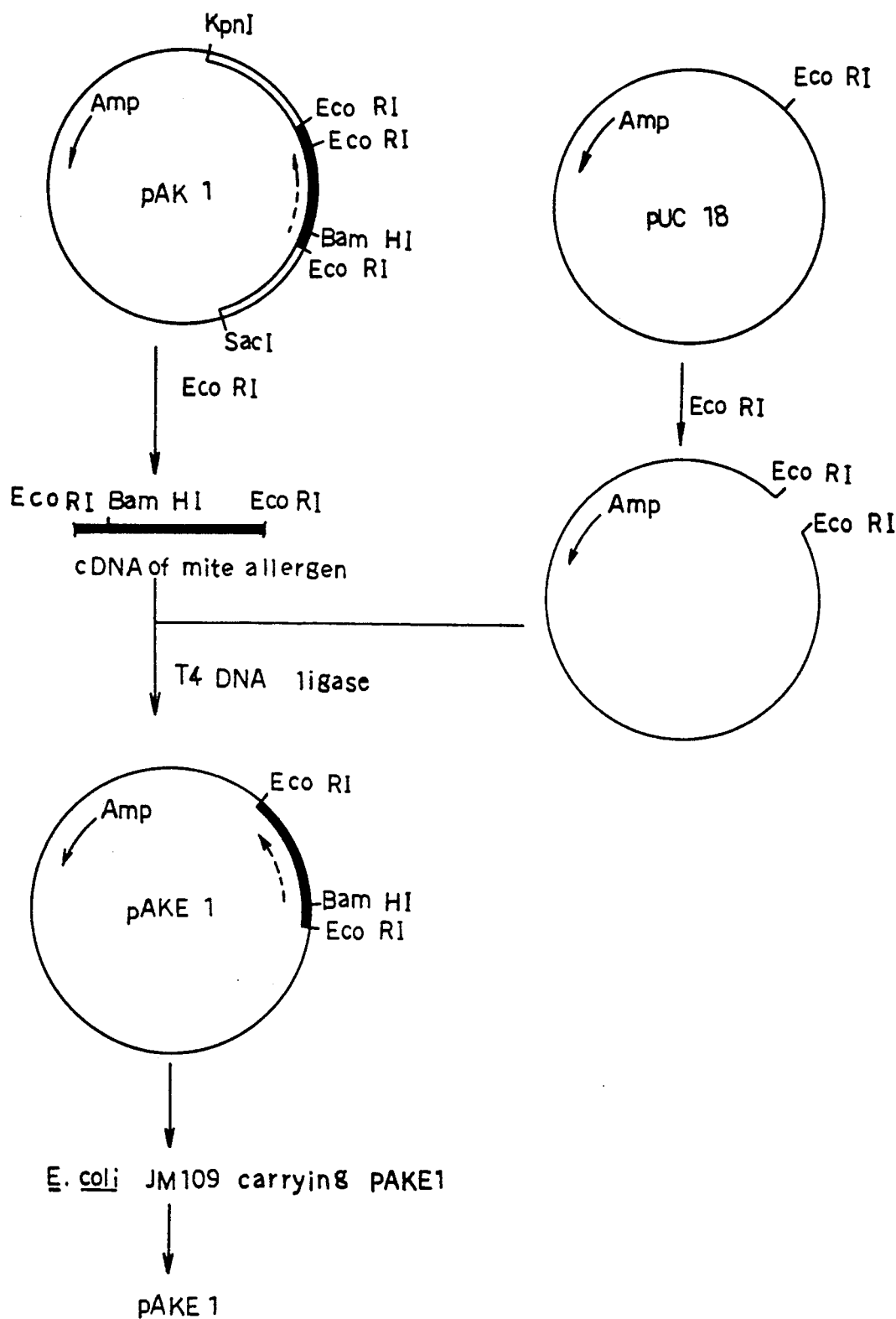
FIG. 5 shows the construction of the recombinant plasmid pAKE1.

The EcoR I digestion fragment of the plasmid pAK 1 was ligated to the same plasmid vector pUC18 at the EcoR I site and transformed into E. coli JM109 in the same manner (FIG. 5).

The obtained recombinant plasmid was named pAKE 1, which was used to draw a restriction enzyme map (940 bp, not including the linker) (FIG. 4). Next, a single-stranded DNA was prepared by a conventional method from the culture supernatants of transformants of the phage vectors M13mp18 and mp19 (produced by Takara Shuzo) containing various fragments obtained by digesting the recombinant plasmids pAK 1 and pAKE 1 with restriction enzymes such as EcoR I and BamH I, and its partial nucleotide sequence was determined by the dideoxy nucleotide chain termination method using Sequenase Version 2.0 (produced by Toyobo Ltd.) (SEQ ID NO:1).

Through repeated investigation of the nucleotide sequence by the same method, a nucleotide sequence of about 1.1 kbp (not including the linker) containing the above-mentioned nucleotide sequence (SEQ ID NO:1) was determined (SEQ ID NO:2).

EXAMPLE 9

Construction of high expression vector

Figure 6:
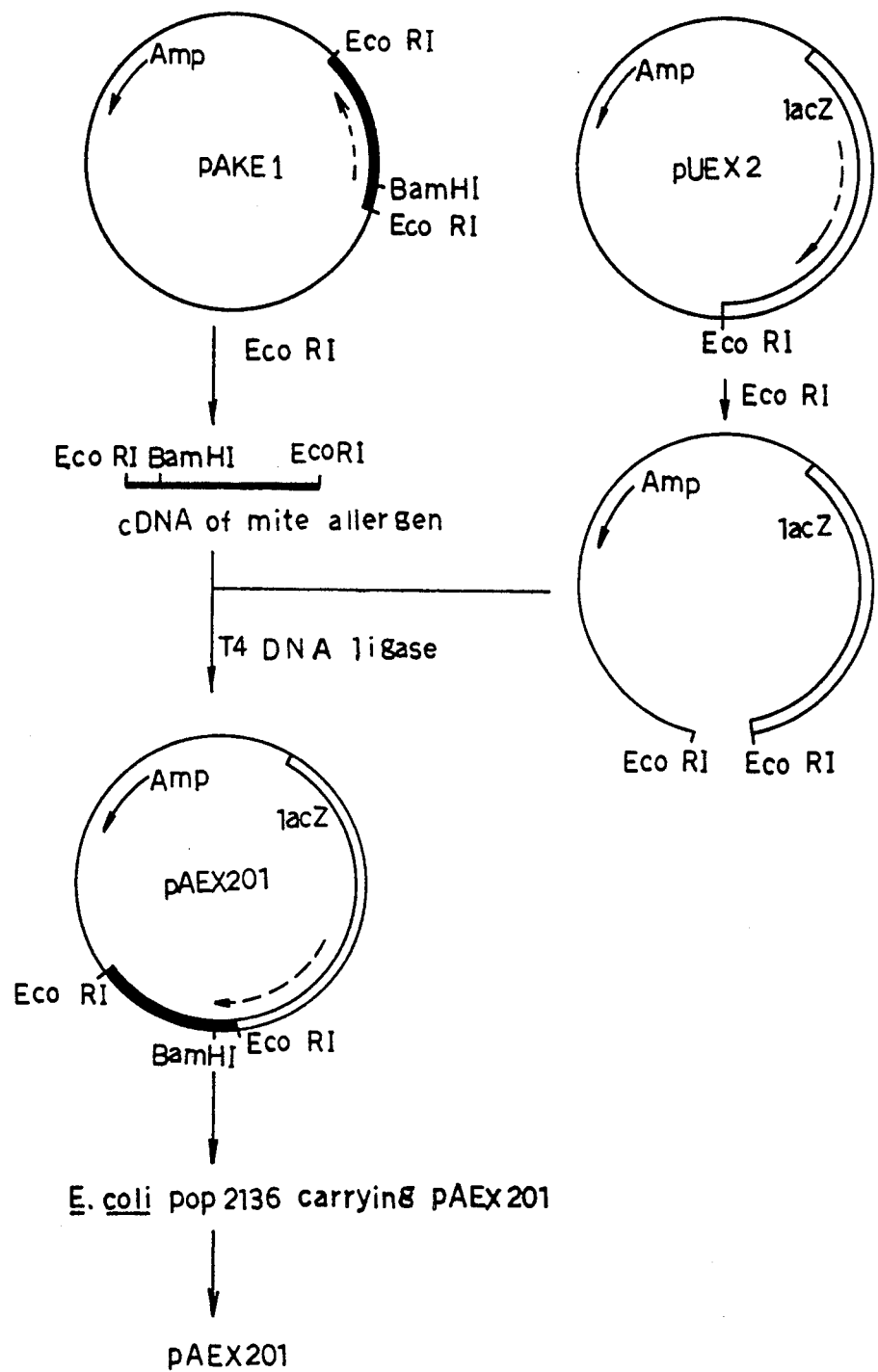
FIG. 6 shows the construction of the recombinant plasmid pAEX201.

The EcoR I digestion fragment (940 bp) of the recombinant plasmid pAKE 1 was subjected to agarose gel electrophoresis and extracted using the Geneclean II kit (produced by BIO 101). This extract was ligated to the vector pUEX 2 (produced by Amersham), previously cleaved by EcoR I digestion, so that the frame fit to the direction of translation (FIG. 6).

EXAMPLE 10

Expression as fused protein

The recombinant plasmid obtained in Example 9 was named pAEX201, which was transformed into *E. coli* pop2136 (produced by Amersham).

Figure 7:
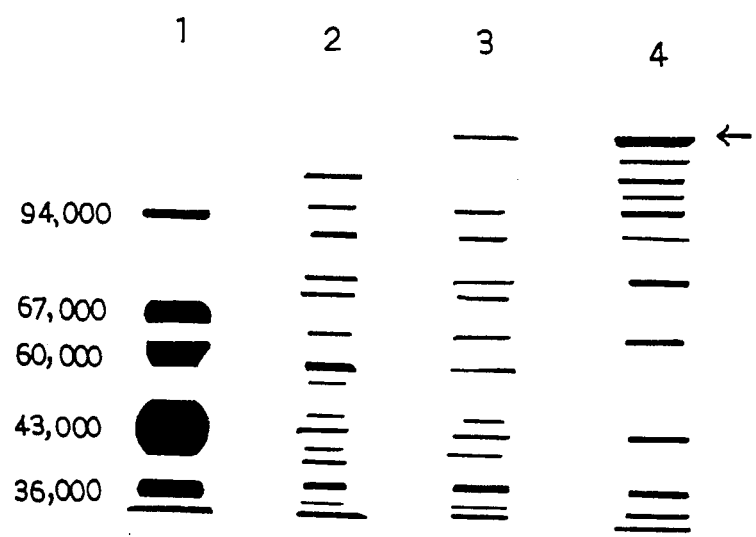
FIG. 7 shows the results of SDS-PAGE analysis of the mite allergen fused protein expressed by pAEX201 in the host E. coli pop2136, in which lane 1 shows the results for a molecular marker; lane 2 shows the results for the total protein of E. coli pop2136 cells carrying the plasmid pUEX2; lane 3 shows the results for the total protein of E. coli pop2136 cells carrying the plasmid pAEX201; and lane 4 shows the results for the protein localized in E. coli pop2136 membrane carrying the plasmid pAEX201 (the recombinant mite allergen is indicated with an arrow).

This transformant was subjected to shaking culture in 500 ml of an SBA liquid medium (2.4% Bacto yeast extract, 1.2% Bacto polypeptone, 0.5% glycerol, 0.1M potassium phosphate, pH 7.5, 50 mg/ml ampicillin) at 28° C. until the OD value at 600 nm became 0.6. After an equal amount of SBA medium maintained at 56° C. was added, shaking culture was continued at 42° C. for additional 90 minutes. An appropriate amount of fresh SBA was added at appropriate times so that the OD value was maintained between 0.6 and 1.0 during the inductive synthesis of fused protein by this temperature shift to 42° C. After completion of the cultivation, the culture broth was centrifuged. Cells were harvested, washed with sterile water and were suspended in 10 ml of a solution containing protease inhibitors [0.1M Tris-HCl, pH 7.5, 1 mM EDTA, 0.1 mM phenylmethanesulfonyl fluoride, 1 mM iodoacetic acid, 5 mM 1,2-epoxy-3-(p-nitrophenoxy)-propane]. This suspension was subjected to 10 cycles of 10-20 kHz ultrasonication for 1 minute to disrupt the cells. After centrifugation, the pellet was suspended in 10 ml of a 0.02% SDS solution. After re-centrifugation, the pellet-forming membrane-localized protein was completely dissolved in 10 ml of a 2% SDS solution. The lyophilized product of this extract was analyzed by SDS-PAGE. The results are shown in FIG. 7.

EXAMPLE 11

Purification of recombinant mite allergen fused protein

Figure 8:
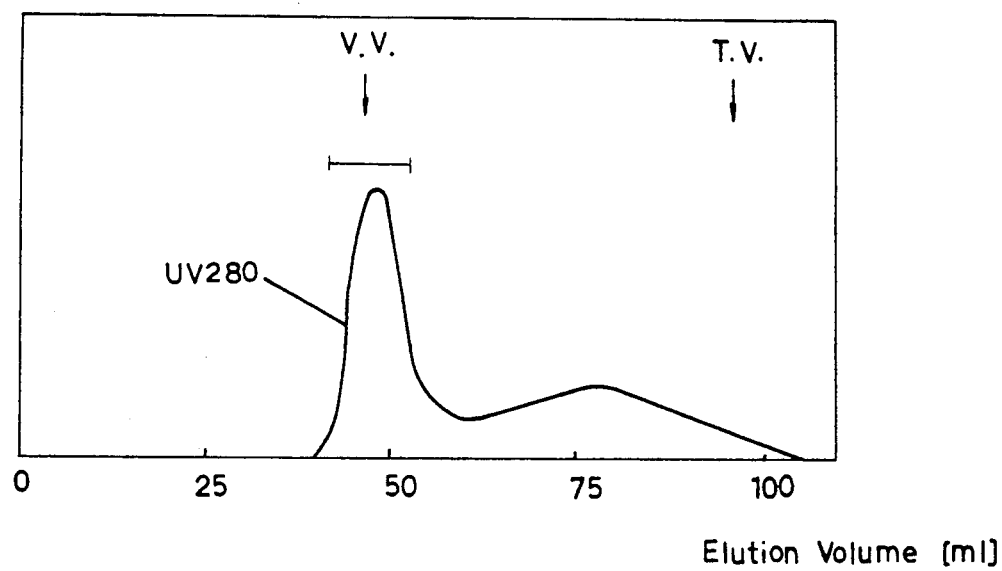
FIG. 8 shows the results of gel filtration and SDS removal for the mite allergen fused protein using a couple of Ultrogel AcA 44 and AG 11A8 columns.

The yield of the lyophilization product of the extract was 122 mg from 500 ml of the culture broth. Five mg of the lyophilization product was dissolved in 500 μl of water, and this solution was applied to a couple of columns of Ultrogel AcA 44 (produced by LKB, 1.4×50 cm)+AG 11A8 (produced by Bio-Rad, 1.4×14 cm) and developed using deionized water as a developing solvent at a flow rate of 10 ml/hr, and the fraction eluted in void volume was collected (FIG. 8). The yield of the lyophilization product of this fraction was 0.6 mg. The lyophilization product was then passed through an anti-β-galactosidase antibody immobilized affinity column and then purified using an anti-mite-body antibody immobilized affinity column. The anti-β-galactosidase antibody immobilized affinity column was prepared by immobilizing an anti-β-galactosidase antibody (produced by 5Prime→3Prime Inc.) to tresyl GM gel (produced by Kurita Water Industries Ltd.). The anti-mite-body antibody immobilized affinity column was prepared by fractionating the rabbit anti-mite-body antigen serum described in Example 5 with ammonium sulfate, then purifying the ammonium sulfate fraction using a column of protein A and immobilizing it onto tresyl GM gel.

EXAMPLE 12

Histamine release test using purified fused protein

A solution of the purified antigen (1 mg/ml) was diluted to an appropriate volume. To 200 μl of this diluted solution, 200 μl of a suspension of blood cells from a mite asthma patient, washed with Hanks' solution, was added, and reaction was carried out at 37° C. for 30 minutes. After centrifugation at 1400 rpm for 10 minutes, 200 μl of the supernatant was taken. To the supernatant, 10 μl of 60% perchloric acid was added, and this mixture was vigorously stirred and centrifuged at 10000 rpm for 10 minutes to remove the protein. 150 μl of this supernatant was subjected to HPLC to determine the amount of histamine in 100 μl of the supernatant. The total amount of histamine was determined in the same manner as above except that blood cell removal by centrifugation was not conducted.

Figure 9:
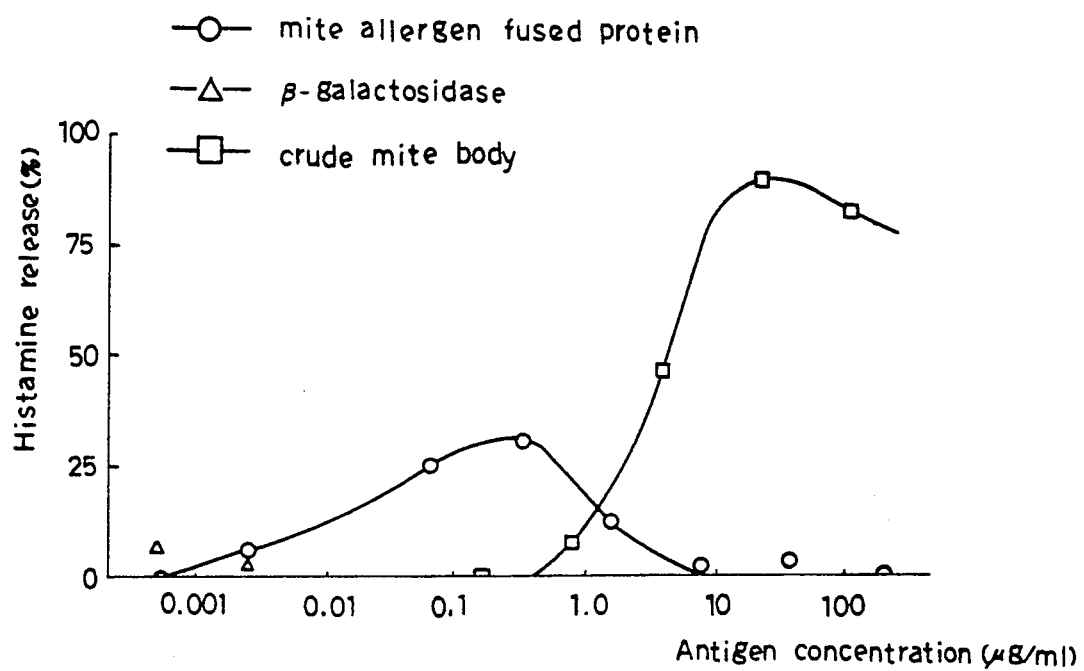
FIG. 9 shows the results of titration of washed blood cells from a mite asthma patient with the mite allergen fused protein.

The obtained results are shown in FIG. 9, in which antigen concentration is plotted on the abscissa and the percent ratio of the released histamine [(amount of released histamine/total amount of histamine)×100] is plotted on the ordinate. Comparing the concentration at the inflexion point reveals that this mite allergen fused protein reacted at a concentration lower by over 200 times than do the crude mite body antigen.

EXAMPLE 13

Preparation of recombinant mite allergen fragment

Using pUEX 2 inserting the 970 bp EcoR I fragment of cDNA, deletion was carried out from the downstream of cDNA with Exonuclease III (produced by Takara Shuzo, Deletion kit for Kilo-Sequence). As a result, 10 kinds of cDNA with a deleted nucleotide chain were obtained as shown in FIG. 10.

These deleted cDNA fragments were each transformed into *E. coli*, and the cells were grown on a nitrocellulose membrane at 28° C. After subsequent inductive expression at 42° C. for 2 hours and lysis with SDS at 100° C., the cell component adsorbed onto the nitrocellulose membrane was visualized for antigen activity by the enzyme-linked immunosorbent method using an anti-mite antigen serum.

Figure 10:
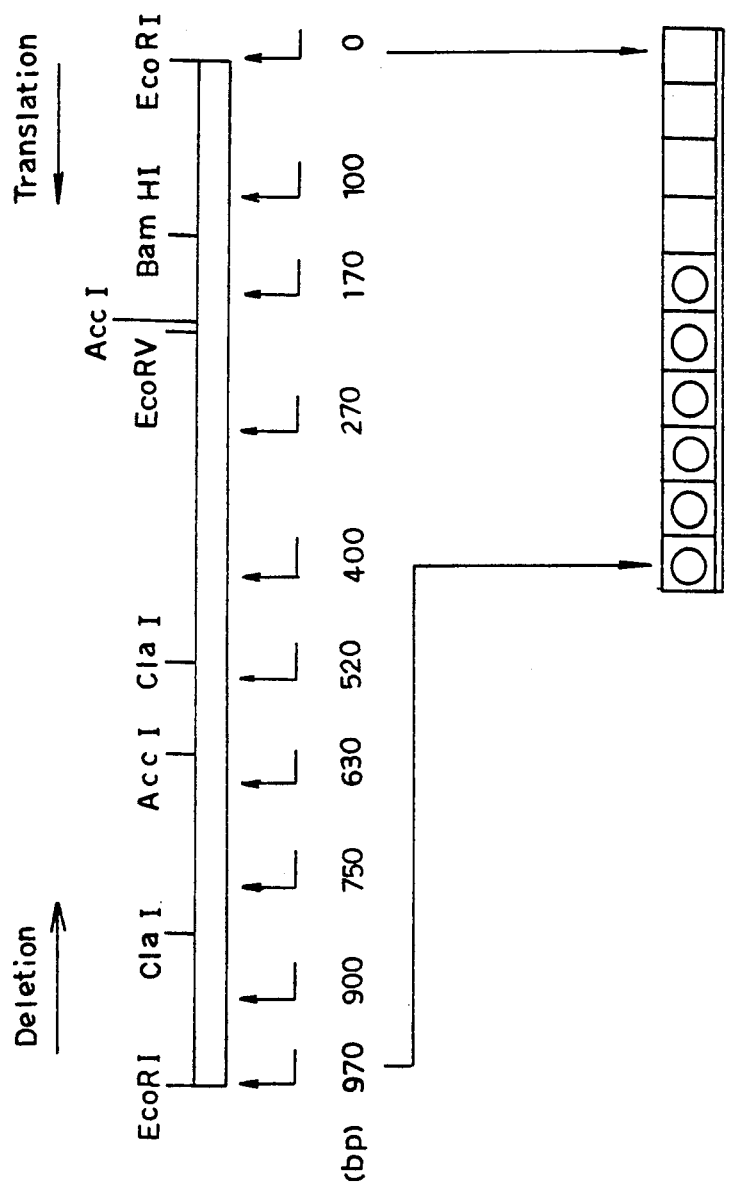
FIG. 10 shows the presence or absence of antigen activity in the deletion mutants of recombinant mite allergen, in which the fragments marked with possess antigen activity.

The results are shown in FIG. 10. It was found that the activity which remained at the 6th spot from the left in the figure after deletion up to about 400 bp mostly disappeared by deletion up to about 270 bp at the 7th spot and the activity completely disappeared by deletion up to about 170 bp at the 8th spot.

This finding suggested that the antibody avidity required at least a region about 170 bp to about 270 bp, about 270 bp to about 400 bp, or about 170 bp to about 400 bp from the upstream; the recombinant mite allergen fragment containing the amino acid sequence of this region could be used as an active ingredient of therapeutic agents and diagnostic reagents for mite allergic diseases.

EXAMPLE 14

Preparation of epitope-containing polypeptide

Figure 11:
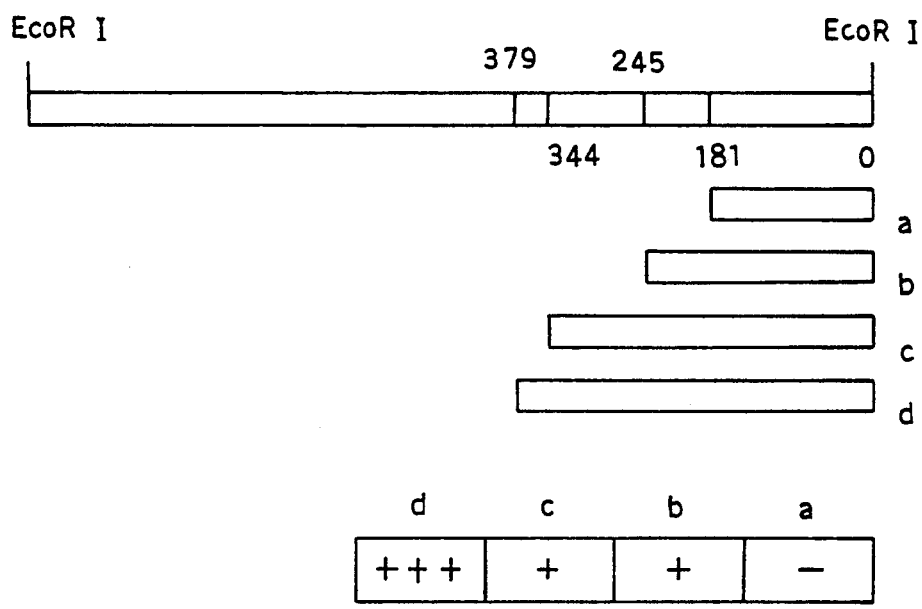
FIG. 11 shows the presence or absence of antigen activity in the deletion mutants of recombinant mite allergen, in which the symbols −, + and +++ indicate the degree of antigen activity in the deletion mutants a, b, c and d.

On the basis of the results of Example 13, epitope regions in the 170–400 bp region were identified as shown in FIG. 11 by adjusting the reaction time of Exonuclease II (produced by Takara Shuzo, Deletion kit for Kilo-Sequence) in the same manner as in Example 13. It was found that two regions of 181–246 bp and 343–378 bp were essential as epitope parts. The nucleotide sequence to the enzyme cleavage point was determined using TAQuence (produced by Toyobo Ltd.). Polypeptides containing the amino acid sequences (SEQ ID NO:3 and SEQ ID NO:4) deduced from these nucleotide sequences can easily be synthesized by a conventional method using, for example, a peptide synthesizer produced by Applied Biosystems.

EXAMPLE 15

Preparation of therapeutic agent for mite allergic diseases

The purified allergen active component is dried, collected in a powder form and used as a hyposensitization therapeutic agent for mite allergy patients.

The allergen active component is dissolved in a 0.9% saline containing 0.5% phenol to a final concentration of 1 mg/ml to yield a stock solution of an antigen for hyposensitization therapy.

EXAMPLE 16

Preparation of diagnostic reagent for mite allergic diseases

The purified allergen active component is dried, collected in a powder form and used as a skin reaction diagnostic reagent for mite allergic diseases and as a titrating reagent for the diagnosis of mite allergy.

The skin reaction diagnostic reagent is prepared by 200,000-fold diluting the allergen active component in a 0.9% physiological saline containing 0.5% phenol.

The titrating reagent for the diagnosis of mite allergy was prepared by dissolving the allergen active component in Hanks' buffer solution at a concentration of 1 mg/ml to yield a stock solution of a reagent for histamine release titration and diluting the stock solution.

---

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 249 base pairs
      ( B ) TYPE: nucleic acid
      ( C ) STRANDEDNESS: double
      ( D ) TOPOLOGY: linear ( i i ) MOLECULE TYPE: cDNA to mRNA ( v i ) ORIGINAL SOURCE:
      ( A ) ORGANISM: Dermatophagoides farinae
      ( F ) TISSUE TYPE: mite body ( i x ) FEATURE:
      ( A ) NAME/KEY: CDS
      ( B ) LOCATION: 1..249
      ( D ) OTHER INFORMATION: /product="mite body allergen"

( x i ) SEQUENCE DESCRIPTION: SEQ ID NO:1:

```
TTT  GTC  ATG  AAA  CGA  GAA  CCA  TTG  CGA  TTC  AGA  GAC  ATC  ACT  GTC  GAA       48
Phe  Val  Met  Lys  Arg  Glu  Pro  Leu  Arg  Phe  Arg  Asp  Ile  Thr  Val  Glu
 1              5                        10                      15

GGA  AAC  GAA  AAT  GCC  TAT  ATC  AAA  AAT  GGC  AAA  CTT  CAT  TTG  TCG  CTT       96
Gly  Asn  Glu  Asn  Ala  Tyr  Ile  Lys  Asn  Gly  Lys  Leu  His  Leu  Ser  Leu
                  20                        25                      30

ATG  GAT  CCG  TCA  ACA  TTG  AGT  TTA  GTC  ACG  AAA  GCC  GAT  GGA  AAA  ATC      144
Met  Asp  Pro  Ser  Thr  Leu  Ser  Leu  Val  Thr  Lys  Ala  Asp  Gly  Lys  Ile
          35                        40                      45

GAC  ATG  ACA  GTA  GAC  TTG  ATA  TCG  CCA  GTC  ACA  AAA  CGT  GCA  TCG  TTG      192
Asp  Met  Thr  Val  Asp  Leu  Ile  Ser  Pro  Val  Thr  Lys  Arg  Ala  Ser  Leu
          50                        55                      60

AAA  ATT  GAT  TCA  AAG  AAA  TAC  AAC  CTT  TTC  CAT  GAA  GGT  GAA  TTG  AGT      240
Lys  Ile  Asp  Ser  Lys  Lys  Tyr  Asn  Leu  Phe  His  Glu  Gly  Glu  Leu  Ser
 65                       70                        75                      80
```

```
GCA TCG ATC                                                                                              249
Ala Ser Ile ( 2 ) INFORMATION FOR SEQ ID NO:2:

( i ) SEQUENCE CHARACTERISTICS:
                ( A ) LENGTH: 83 amino acids
                ( B ) TYPE: amino acid
                ( D ) TOPOLOGY: linear ( i i ) MOLECULE TYPE: protein ( x i ) SEQUENCE DESCRIPTION: SEQ ID NO:2:

Phe Val Met Lys Arg Glu Pro Leu Arg Phe Arg Asp Ile Thr Val Glu
  1           5                   10                  15

Gly Asn Glu Asn Ala Tyr Ile Lys Asn Gly Lys Leu His Leu Ser Leu
             20                  25                  30

Met Asp Pro Ser Thr Leu Ser Leu Val Thr Lys Ala Asp Gly Lys Ile
         35                  40                  45

Asp Met Thr Val Asp Leu Ile Ser Pro Val Thr Lys Arg Ala Ser Leu
     50                  55                  60

Lys Ile Asp Ser Lys Lys Tyr Asn Leu Phe His Glu Gly Glu Leu Ser
 65                  70                  75                  80

Ala Ser Ile ( 2 ) INFORMATION FOR SEQ ID NO:3:

( i ) SEQUENCE CHARACTERISTICS:
                ( A ) LENGTH: 1023 base pairs
                ( B ) TYPE: nucleic acid
                ( C ) STRANDEDNESS: double
                ( D ) TOPOLOGY: linear ( i i ) MOLECULE TYPE: cDNA to mRNA ( v i ) ORIGINAL SOURCE:
                ( A ) ORGANISM: Dermatophagoides farinae
                ( F ) TISSUE TYPE: mite body ( i x ) FEATURE:
                ( A ) NAME/KEY: CDS
                ( B ) LOCATION: 1..1023
                ( D ) OTHER INFORMATION: /product="mite body allergen"

( x i ) SEQUENCE DESCRIPTION: SEQ ID NO:3:

TTT GTC ATG AAA CGA GAA CCA TTG CGA TTC AGA GAC ATC ACT GTC GAA      48
Phe Val Met Lys Arg Glu Pro Leu Arg Phe Arg Asp Ile Thr Val Glu
  1           5                   10                  15

GGA AAC GAA AAT GCC TAT ATC AAA AAT GGC AAA CTT CAT TTG TCG CTT      96
Gly Asn Glu Asn Ala Tyr Ile Lys Asn Gly Lys Leu His Leu Ser Leu
             20                  25                  30

ATG GAT CCG TCA ACA TTG AGT TTA GTC ACG AAA GCC GAT GGA AAA ATC     144
Met Asp Pro Ser Thr Leu Ser Leu Val Thr Lys Ala Asp Gly Lys Ile
         35                  40                  45

GAC ATG ACA GTA GAC TTG ATA TCG CCA GTC ACA AAA CGT GCA TCG TTG     192
Asp Met Thr Val Asp Leu Ile Ser Pro Val Thr Lys Arg Ala Ser Leu
     50                  55                  60

AAA ATT GAT TCA AAG AAA TAC AAC CTT TTC CAT GAA GGT GAA TTG AGT     240
Lys Ile Asp Ser Lys Lys Tyr Asn Leu Phe His Glu Gly Glu Leu Ser
 65                  70                  75                  80

GCA TCG ATC GTA AAC CCA CGA TTG TCA TGG CAT CAA TAC ACG AAA CGC     288
Ala Ser Ile Val Asn Pro Arg Leu Ser Trp His Gln Tyr Thr Lys Arg
             85                  90                  95

GAT TCT CGT GAA TAC AAG AGT GAT GTA GAA CTA TCG TTG CGA TCG TCG     336
Asp Ser Arg Glu Tyr Lys Ser Asp Val Glu Leu Ser Leu Arg Ser Ser
            100                 105                 110
```

| | | | | | | | | | | | | | | | | |
|---|---|---|---|---|---|---|---|---|---|---|---|---|---|---|---|---|
| GAC | ATT | GCT | CTC | AAG | ATT | ACG | ATG | CCT | GAT | TAT | AAT | TCG | AAA | ATT | CAT | 384 |
| Asp | Ile | Ala 115 | Leu | Lys | Ile | Thr | Met 120 | Pro | Asp | Tyr | Asn | Ser 125 | Lys | Ile | His | |
| TAT | TCA | CGA | CAA | GGT | GAT | CAA | ATC | AAC | ATG | GAC | ATC | GAT | GGT | ACA | TTG | 432 |
| Tyr | Ser 130 | Arg | Gln | Gly | Asp | Gln 135 | Ile | Asn | Met | Asp | Ile 140 | Asp | Gly | Thr | Leu | |
| ATC | GAA | GGT | CAT | GCA | CAA | GGA | ACC | ATC | AGA | GAA | GGT | AAA | ATC | CAC | ATT | 480 |
| Ile 145 | Glu | Gly | His | Ala | Gln 150 | Gly | Thr | Ile | Arg | Glu 155 | Gly | Lys | Ile | His | Ile 160 | |
| AAA | GGT | AGA | CAA | ACT | GAT | TTC | GAG | ATC | GAA | TCC | AAC | TAC | CGA | TAC | GAA | 528 |
| Lys | Gly | Arg | Gln | Thr 165 | Asp | Phe | Glu | Ile | Glu 170 | Ser | Asn | Tyr | Arg | Tyr 175 | Glu | |
| GAT | GGC | AAA | CTA | ATC | ATC | GAA | CCG | GTC | AAG | AGT | GAA | AAT | GGC | AAA | TTG | 576 |
| Asp | Gly | Lys | Leu 180 | Ile | Ile | Glu | Pro | Val 185 | Lys | Ser | Glu | Asn | Gly 190 | Lys | Leu | |
| GAA | GGC | GTT | CTT | TCC | CGT | AAG | GTG | CCA | TCA | CAT | CTG | ACA | CTA | GAA | ACA | 624 |
| Glu | Gly | Val 195 | Leu | Ser | Arg | Lys | Val 200 | Pro | Ser | His | Leu | Thr 205 | Leu | Glu | Thr | |
| CCA | CGA | GTC | AAG | ATG | AAT | ATG | AAA | TAT | GAT | CGA | TAT | GCA | CCA | GTC | AAA | 672 |
| Pro | Arg 210 | Val | Lys | Met | Asn | Met 215 | Lys | Tyr | Asp | Arg | Tyr 220 | Ala | Pro | Val | Lys | |
| GTG | TTC | AAA | TTG | GAT | TAT | GAT | GGC | ATC | CAC | TTC | GAG | AAA | CAT | ACC | GAT | 720 |
| Val 225 | Phe | Lys | Leu | Asp | Tyr 230 | Asp | Gly | Ile | His | Phe 235 | Glu | Lys | His | Thr | Asp 240 | |
| ATT | GAA | TAC | GAA | CCT | GGC | GTT | CGA | TAC | AAG | ATC | ATC | GGC | AAT | GGA | AAA | 768 |
| Ile | Glu | Tyr | Glu | Pro 245 | Gly | Val | Arg | Tyr | Lys 250 | Ile | Ile | Gly | Asn | Gly 255 | Lys | |
| CTC | AAG | GAT | GAT | GGC | CGC | CAC | TAT | TCT | ATC | GAT | GTG | CAA | GGT | ATT | CCA | 816 |
| Leu | Lys | Asp | Asp 260 | Gly | Arg | His | Tyr | Ser 265 | Ile | Asp | Val | Gln | Gly 270 | Ile | Pro | |
| CGC | AAA | GCA | TTC | AAT | CTG | GAC | GCT | GAC | TTG | ATG | GAT | TTC | AAA | CTG | AAA | 864 |
| Arg | Lys | Ala 275 | Phe | Asn | Leu | Asp | Ala 280 | Asp | Leu | Met | Asp | Phe 285 | Lys | Leu | Lys | |
| GTG | AGC | AAG | CCA | GAA | GAT | AGC | AAT | AAA | GCT | CAA | TTC | AGC | TAC | ACA | TTC | 912 |
| Val | Ser 290 | Lys | Pro | Glu | Asp | Ser 295 | Asn | Lys | Ala | Gln | Phe 300 | Ser | Tyr | Thr | Phe | |
| AAC | GAA | TAT | ACC | GAG | ACC | GAA | GAA | TAT | GAA | TTC | GAT | CCA | CAT | CGT | GCC | 960 |
| Asn | Glu | Tyr | Thr | Glu 310 | Thr | Glu | Glu | Tyr | Glu 315 | Phe | Asp | Pro | His | Arg 320 | Ala | |
| Asn 305 | | | | | | | | | | | | | | | | |
| TAT | TAT | GTT | AAT | TGG | TTG | AGT | TCC | ATT | CGC | AAA | TAC | ATC | CAG | AAT | TTC | 1008 |
| Tyr | Tyr | Val | Asn | Trp 325 | Leu | Ser | Ser | Ile | Arg 330 | Lys | Tyr | Ile | Gln | Asn 335 | Phe | |
| ATC | GTC | GAA | GAC | AAC | | | | | | | | | | | | 1023 |
| Ile | Val | Glu | Asp | Asn 340 | | | | | | | | | | | | |

( 2 ) INFORMATION FOR SEQ ID NO:4:

( i ) SEQUENCE CHARACTERISTICS:
        ( A ) LENGTH: 341 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Phe 1 | Val | Met | Lys | Arg 5 | Glu | Pro | Leu | Arg | Phe 10 | Arg | Asp | Ile | Thr | Val 15 | Glu |
| Gly | Asn | Glu | Asn 20 | Ala | Tyr | Ile | Lys | Asn 25 | Gly | Lys | Leu | His | Leu 30 | Ser | Leu |
| Met | Asp | Pro | Ser 35 | Thr | Leu | Ser | Leu | Val 40 | Thr | Lys | Ala | Asp | Gly 45 | Lys | Ile |

| Asp | Met | Thr | Val | Asp | Leu | Ile | Ser | Pro | Val | Thr | Lys | Arg | Ala | Ser | Leu |
| | 50 | | | | 55 | | | | | 60 | | | | | |

| Lys | Ile | Asp | Ser | Lys | Lys | Tyr | Asn | Leu | Phe | His | Glu | Gly | Glu | Leu | Ser |
| 65 | | | | | 70 | | | | | 75 | | | | | 80 |

| Ala | Ser | Ile | Val | Asn | Pro | Arg | Leu | Ser | Trp | His | Gln | Tyr | Thr | Lys | Arg |
| | | | | 85 | | | | | 90 | | | | | 95 | |

| Asp | Ser | Arg | Glu | Tyr | Lys | Ser | Asp | Val | Glu | Leu | Ser | Leu | Arg | Ser | Ser |
| | | | 100 | | | | | | 105 | | | | 110 | | |

| Asp | Ile | Ala | Leu | Lys | Ile | Thr | Met | Pro | Asp | Tyr | Asn | Ser | Lys | Ile | His |
| | | | 115 | | | | | 120 | | | | 125 | | | |

| Tyr | Ser | Arg | Gln | Gly | Asp | Gln | Ile | Asn | Met | Asp | Ile | Asp | Gly | Thr | Leu |
| | | | 130 | | | | 135 | | | | | 140 | | | |

| Ile | Glu | Gly | His | Ala | Gln | Gly | Thr | Ile | Arg | Glu | Gly | Lys | Ile | His | Ile |
| 145 | | | | | 150 | | | | | 155 | | | | | 160 |

| Lys | Gly | Arg | Gln | Thr | Asp | Phe | Glu | Ile | Glu | Ser | Asn | Tyr | Arg | Tyr | Glu |
| | | | | 165 | | | | | 170 | | | | | 175 | |

| Asp | Gly | Lys | Leu | Ile | Ile | Glu | Pro | Val | Lys | Ser | Glu | Asn | Gly | Lys | Leu |
| | | | 180 | | | | | 185 | | | | | 190 | | |

| Glu | Gly | Val | Leu | Ser | Arg | Lys | Val | Pro | Ser | His | Leu | Thr | Leu | Glu | Thr |
| | | | 195 | | | | | 200 | | | | | 205 | | |

| Pro | Arg | Val | Lys | Met | Asn | Met | Lys | Tyr | Asp | Arg | Tyr | Ala | Pro | Val | Lys |
| | 210 | | | | | 215 | | | | | 220 | | | | |

| Val | Phe | Lys | Leu | Asp | Tyr | Asp | Gly | Ile | His | Phe | Glu | Lys | His | Thr | Asp |
| 225 | | | | | 230 | | | | | 235 | | | | | 240 |

| Ile | Glu | Tyr | Glu | Pro | Gly | Val | Arg | Tyr | Lys | Ile | Ile | Gly | Asn | Gly | Lys |
| | | | | 245 | | | | | 250 | | | | | 255 | |

| Leu | Lys | Asp | Asp | Gly | Arg | His | Tyr | Ser | Ile | Asp | Val | Gln | Gly | Ile | Pro |
| | | | 260 | | | | | 265 | | | | | 270 | | |

| Arg | Lys | Ala | Phe | Asn | Leu | Asp | Ala | Asp | Leu | Met | Asp | Phe | Lys | Leu | Lys |
| | | 275 | | | | | 280 | | | | | 285 | | | |

| Val | Ser | Lys | Pro | Glu | Asp | Ser | Asn | Lys | Ala | Gln | Phe | Ser | Tyr | Thr | Phe |
| | 290 | | | | | 295 | | | | | 300 | | | | |

| Asn | Glu | Tyr | Thr | Glu | Thr | Glu | Glu | Tyr | Glu | Phe | Asp | Pro | His | Arg | Ala |
| 305 | | | | | 310 | | | | | 315 | | | | | 320 |

| Tyr | Tyr | Val | Asn | Trp | Leu | Ser | Ser | Ile | Arg | Lys | Tyr | Ile | Gln | Asn | Phe |
| | | | | 325 | | | | | 330 | | | | | 335 | |

| Ile | Val | Glu | Asp | Asn |
| | | | 340 | |

( 2 ) INFORMATION FOR SEQ ID NO:5:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Dermatophagoides farinae
        ( F ) TISSUE TYPE: mite body ( i x ) FEATURE:
        ( A ) NAME/KEY: CDS
        ( B ) LOCATION: 1..66
        ( D ) OTHER INFORMATION: /product="mite body allergen"

( x i ) SEQUENCE DESCRIPTION: SEQ ID NO:5:

| ATG | ACA | GTA | GAC | TTG | ATA | TCG | CCA | GTC | ACA | AAA | CGT | GCA | TCG | TTG | AAA | 48 |
| Met | Thr | Val | Asp | Leu | Ile | Ser | Pro | Val | Thr | Lys | Arg | Ala | Ser | Leu | Lys | |
| 1 | | | | 5 | | | | | 10 | | | | | 15 | | |

```
ATT GAT TCA AAG AAA TAC                                                              6 6
Ile Asp Ser Lys Lys Tyr
              2 0
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Thr Val Asp Leu Ile Ser Pro Val Thr Lys Arg Ala Ser Leu Lys
 1               5                   1 0                  1 5
Ile Asp Ser Lys Lys Tyr
              2 0
```

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Dermatophagoides farinae
        ( F ) TISSUE TYPE: mite body ( i x ) FEATURE:
        ( A ) NAME/KEY: CDS
        ( B ) LOCATION: 1..36
        ( D ) OTHER INFORMATION: /product="mite body allergen"

( x i ) SEQUENCE DESCRIPTION: SEQ ID NO:7:

```
GAT GTA GAA CTA TCG TTG CGA TCG TCG GAC ATT GCT                                      3 6
Asp Val Glu Leu Ser Leu Arg Ser Ser Asp Ile Ala
 1               5                   1 0
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asp Val Glu Leu Ser Leu Arg Ser Ser Asp Ile Ala
 1               5                   1 0
```

What is claimed is:

1. A substantially pure recombinant mite allergen obtainable by expression of a mite-body-derived gene fragment, which contains the partial amino acid sequence shown in SEQ ID NO:2:

Phe Val Met Lys Arg Glu Pro Leu Arg Phe Arg

Asp Ile Thr Val Glu

Gly Asn Glu Asn Ala Tyr Ile Lys Asn Gly Lys

Leu His Leu Ser Leu

Met Asp Pro Ser Thr Leu Ser Leu Val Thr Lys

Ala Asp Gly Lys Ile

Asp Met Thr Val Asp Leu Ile Ser Pro Val Thr

Lys Arg Ala Ser Leu

Lys Ile Asp Ser Lys Lys Tyr Asn Leu Phe His

Glu Gly Glu Leu Ser

Ala Ser Ile.

2. A substantially pure recombinant mite allergen obtainable by expression of a mite-body-derived gene fragment, which contains the partial amino acid sequence shown in SEQ ID NO:4:

Phe Val Met Lys Arg Glu Pro Leu Arg Phe
  Arg Asp Ile Thr Val Glu
Gly Asn Glu Asn Ala Tyr Ile Lys Asn Gly
  Lys Leu His Leu Ser Leu
Met Asp Pro Ser Thr Leu Ser Leu Val Thr
  Lys Ala Asp Gly Lys Ile
Asp Met Thr Val Asp Leu Ile Ser Pro Val
  Thr Lys Arg Ala Ser Leu
Lys Ile Asp Ser Lys Lys Tyr Asn Leu Phe
  His Glu Gly Glu Leu Ser
Ala Ser Ile Val Asn Pro Arg Leu Ser Trp
  His Gln Tyr Thr Lys Arg
Asp Ser Arg Glu Tyr Lys Ser Asp Val Glu
  Leu Ser Leu Arg Ser Ser
Asp Ile Ala Leu Lys Ile Thr Met Pro Asp
  Tyr Asn Ser Lys Ile His
Tyr Ser Arg Gln Gly Asp Gln Ile Asn Met
  Asp Ile Asp Gly Thr Leu
Ile Glu Gly His Ala Gln Gly Thr Ile Arg
  Glu Gly Lys Ile His Ile
Lys Gly Arg Gln Thr Asp Phe Glu Ile Glu
  Ser Asn Tyr Arg Tyr Glu
Asp Gly Lys Leu Ile Ile Glu Pro Val Lys
  Ser Glu Asn Gly Lys Leu
Glu Gly Val Leu Ser Arg Lys Val Pro Ser
  His Leu Thr Leu Glu Thr
Pro Arg Val Lys Met Asn Met Lys Tyr Asp
  Arg Tyr Ala Pro Val Lys
Val Phe Lys Leu Asp Tyr Asp Gly Ile His
  Phe Glu Lys His Thr Asp
Ile Glu Tyr Glu Pro Gly Val Arg Tyr Lys
  Ile Ile Gly Asn Gly Lys
Leu Lys Asp Asp Gly Arg His Tyr Ser Ile
  Asp Val Gln Gly Ile Pro
Arg Lys Ala Phe Asn Leu Asp Ala Asp Leu
  Met Asp Phe Lys Leu Lys
Val Ser Lys Pro Glu Asp Ser Asn Lys Ala
  Gln Phe Ser Tyr Thr Phe
Asn Glu Tyr Thr Glu Thr Glu Glu Tyr Glu
  Phe Asp Pro His Arg Ala

-continued
Tyr Tyr Val Asn Trp Leu Ser Ser Ile Arg
  Lys Tyr Ile Gln Asn Phe
Ile Val Glu Asp Asn.

3. A recombinant mite allergen according to claim 1 wherein said gene fragment is derived from *Dermatophagoides farinae*.

4. A recombinant mite allergen according to claim 1, wherein the molecular weight of said allergen is about 40,000 as determined by SDS-PAGE.

5. A recombinant mite allergen according to claim 1, wherein the total nucleotide chain length of the cDNA of said allergen is about 1.2 kbp as determined by agarose electrophoresis, and which is obtainable by expression of a gene fragment containing the restriction enzyme map shown in FIG. 4.

6. A fused recombinant mite allergen, wherein the recombinant mite allergen of claim 1 is fused with another protein.

7. A fused recombinant mite allergen according to claim 6, wherein said protein is β-galactosidase.

8. A substantially pure mite allergen fragment containing at least an amino acid sequence encoded in the region of about 170 bp to about 270 bp, about 270 bp to about 400 bp, or about 170 bp to about 400 bp from the translation start in the restriction map shown in FIG. 10.

9. A substantially pure polypeptide having an epitope contained in an amino acid sequence encoded by a DNA fragment as shown in the restriction map shown in FIG. 10, said DNA fragment being a cDNA obtained from *Dermatofagoides farinae*, said DNA fragment being selected from the group consisting of 170 bp to 270 bp from the start of translation, 270 bp to 400 bp from the start of translation and 170 to 400 bp from the start of translation.

10. A polypeptide according to claim 9, containing the amino acid sequence shown in SEQ ID NO:6:Met Thr Val Asp Leu Ile Ser Pro Val Thr Lys Arg Ala Ser Leu Lys Ile Asp Ser Lys Lys Tyr.

11. A polypeptide according to claim 9, containing the amino acid sequence shown in SEQ ID NO:8:Asp Val Glu Leu Ser Leu Arg Ser Ser Asp Ile Ala.

12. A diagnostic reagent for mite allergic diseases, which comprises as the active ingredient a diagnostically effective amount of the recombinant mite allergen of claim 1.

13. A diagnostic reagent for mite allergic diseases, which comprises as the active ingredient a diagnostically effective amount of the mite allergen fragment of claim 8.

14. A diagnostic reagent for mite allergic diseases, which comprises as the active ingredient a diagnostically effective amount of the polypeptide of claim 10.

15. A substantially pure recombinant mite allergen, wherein said recombinant mite allergen has the amino acid sequence shown in SEQ. ID. No. 1 and is produced by a process comprising the steps of:
  (a) expressing a fusion gene composed of a mite-body-derived gene ligated to a gene encoding at least a second protein;
  (b) collecting a fusion protein composed of a mite-body-derived allergen and said second protein obtained from step (a);

(c) separating said second protein from said mite-body-derived allergen;

(d) collecting said mite-body-derived allergen.

16. A substantially pure recombinant mite allergen, wherein said recombinant mite allergen has the amino acid sequence shown in SEQ. ID. No. 2 and is produced by a process comprising the steps of:

(a) expressing a fusion gene composed of a mite-body-derived gene ligated to a gene encoding at least a second protein;

(b) collecting a fusion protein composed of a mite-body-derived allergen and said second protein obtained from step (a);

(c) separating said second protein from said mite-body-derived allergen;

(d) collecting said mite-body-derived allergen.

* * * * *